United States Patent
Steinmetz

(10) Patent No.: US 12,251,410 B2
(45) Date of Patent: *Mar. 18, 2025

(54) ANTICANCER TRAIL-TARGETED PLANT VIRUS PARTICLES

(71) Applicant: CASE WESTERN RESERVE UNIVERSITY, Cleveland, OH (US)

(72) Inventor: Nicole F. Steinmetz, San Diego, CA (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/209,138

(22) Filed: Jun. 13, 2023

(65) Prior Publication Data

US 2024/0115635 A1   Apr. 11, 2024

Related U.S. Application Data

(63) Continuation of application No. 16/614,676, filed as application No. PCT/US2018/033203 on May 17, 2018, now Pat. No. 11,672,840.

(60) Provisional application No. 62/507,603, filed on May 17, 2017.

(51) Int. Cl.
| | |
|---|---|
| *A61K 35/76* | (2015.01) |
| *A61K 31/282* | (2006.01) |
| *A61K 31/436* | (2006.01) |
| *A61K 38/17* | (2006.01) |
| *A61K 47/69* | (2017.01) |
| *A61P 35/04* | (2006.01) |
| *C12N 7/00* | (2006.01) |

(52) U.S. Cl.
CPC ............ *A61K 35/76* (2013.01); *A61K 31/282* (2013.01); *A61K 31/436* (2013.01); *A61K 38/1793* (2013.01); *A61K 47/6901* (2017.08); *A61P 35/04* (2018.01); *C12N 7/00* (2013.01)

(58) Field of Classification Search
CPC .............. A61K 47/6901; A61K 31/282; A61K 31/436; A61K 38/1793; A61P 35/04; A61P 35/76; C12N 7/00
USPC ....................................................... 424/93.2
See application file for complete search history.

(56) References Cited

U.S. PATENT DOCUMENTS

| | | | | |
|---|---|---|---|---|
| 7,959,928 | B2 * | 6/2011 | Bachmann | A61P 37/02 |
| | | | | 435/235.1 |
| 9,925,281 | B2 | 3/2018 | Steinmetz et al. | |
| 10,086,095 | B2 | 10/2018 | Steinmetz et al. | |
| 10,207,014 | B2 | 2/2019 | Steinmetz et al. | |
| 10,478,510 | B2 | 11/2019 | Steinmetz | |
| 11,020,497 | B2 | 6/2021 | Steinmetz et al. | |
| 11,253,610 | B2 | 2/2022 | Steinmetz | |
| 11,672,840 | B2 * | 6/2023 | Steinmetz | A61K 47/6901 |
| | | | | 424/93.2 |
| 2005/0019270 | A1 | 1/2005 | Finlay et al. | |
| 2007/0248617 | A1 | 10/2007 | Bachmann et al. | |
| 2010/0183504 | A1 | 7/2010 | Chen | |
| 2015/0033418 | A1 | 1/2015 | Lommel et al. | |
| 2015/0265696 | A1 | 9/2015 | Gourapura et al. | |
| 2020/0179468 | A1 | 6/2020 | Steinmetz | |
| 2022/0211881 | A1 | 7/2022 | Steinmetz | |

FOREIGN PATENT DOCUMENTS

| | | | |
|---|---|---|---|
| WO | 200118199 | A1 | 3/2001 |
| WO | 2001/0026682 | A2 | 4/2001 |
| WO | 2003092623 | A2 | 11/2003 |
| WO | 2012078069 | A1 | 6/2012 |
| WO | 2013181557 | A1 | 12/2013 |
| WO | 2014059021 | A1 | 4/2014 |
| WO | 2015/0039255 | A1 | 3/2015 |
| WO | 2015/188110 | A1 | 12/2015 |
| WO | 2016019393 | A1 | 2/2016 |
| WO | 2016/149264 | A1 | 9/2016 |
| WO | 2017/004123 | A1 | 1/2017 |

OTHER PUBLICATIONS

Trivedi et al. Trailing TRAIL resistance: novel targets for TRAIL sensitization in cancer cells. Frontiers in Oncology vol. 5, Article 69, p. 1-20, Apr. 2015. (Year: 2015).*
"CWRU researcher to turn plant virus shells against human cancers", The Daily, CWRU Researcher to Turn Plant Virus Shells Against Human Cancers. Case Western Reserve University, Apr. 18, 2016.
Agrawal Arpita et al: "Differential Uptake of Chemically Modified Cowpea Mosaic Virus Nanoparticles in Macrophage Subpopulations Present in Inflammatory and Tumor Microenvironments", BIOMACROMOLECULES, vol. 13, No. 10, Oct. 2012 pp. 3320-3326, XP002780313.
Applicant: Case Western Reserve University; "Cancer Immunotherapy Using Virus Particles"; European Patent Application No. 18764856.3 for Supplementary European Search Report dated Dec. 22, 2020; 8 pgs.
Applicant: Case Western Reserve University; "Cancer Immunotherapy Using Virus Particles"; European Patent Application No. 21201960. 8; Extended European Search Report dated Jan. 19, 2022; 11 pgs.
Brennan Frank R et al: "Cowpea mosaic virus as a vaccine carrier of heterologous antigens", Molecular Biotechnology, vol. 17, No. 1, Jan. 2001 (Jan. 2001), pp. 15-26, XP002780312, ISSN: 1073-6085.
Bruckman et al. (Nano Letters. Mar. 2014; 14: 1551-1558).

(Continued)

*Primary Examiner* — Yih-Horng Shiao
(74) *Attorney, Agent, or Firm* — Tarolli, Sundheim, Covell & Tummino LLP

(57) ABSTRACT

An agent is described that includes a plant virus particle or VLP conjugate to TRAIL. Associating TRAIL with the plant virus particle or VLP serves to both target cancer cells and induce their apoptosis. The agent can therefore be used for a method of treating cancer in a subject.

17 Claims, 11 Drawing Sheets

(56) References Cited

OTHER PUBLICATIONS

Chariou, et al., "Detection and Imaging of Aggressive Cancer Cells Using an Epidermal Growth Factor Receptor (EGFR)-Targeted Filamentous Plant Virus-Based Nanoparticle", Bioconjug Chem. Feb. 18, 2015; 26(2): 262-269.
Chinese Patent Appl. No. 201580063662.6; Chinese Office Action; May 5, 2022; 3 pgs.
Czapar, Anna et al. Tobacco Mosaic Virus Delivery of Phenanthriplatin for Cancer therapy. American Chemical Society. Nano 2016 (10) pp. 4119-4126 (Year: 2016).
Gonzalez Maria J et al: "Interaction of Cowpea Mosaic Virus (CPMV) Nanoparticles with Antigen Presenting Cells In Vitro and In Vivo", PLOS ONE, vol. 4, No. 11, Nov. 2009 (Nov. 2009), XP002780311, ISSN: 1932-6203.
Imamura et al. ("FOXA 1 promotes tumor progression in prostate cancer via the insulin-like growth factor binding protein 3 pathway." (2012)).
Lam, et al. (WIREs Nanomed Nanobiotechnol Jan./Feb. 2018 vol. 10: 1-18).
Le, Duc et al. Biodistribution of Filamentous Plant Virus Nanoparticles: Pepino Mosaic Virus versus Potato Virus X. Biomacromolecules 219 Jan. 14; 20(a): pp. 469-477. (Year 2019).
Le, Duc et al. Chemical addressability of potoato virus X for its applications in bio/nanotechnology. El Sevier. Journal of Structural Biology 200 (2017). pp. 360-368. (Year: 2017).
Le, Duc et al. Potato virus X, a filamentous plant viral nanoparticle for doxorubicin delivery in cancer therapy. Royal Society of Chemistry. Nanoscale, 2017 (9). pp. 2348-2357. (Year 2017).
Lee et al. "Biodegradable Viral Nanoparticle/Polymer Implants Prepared via Melt-Processing", ACS Nano ePub Sep. 13, 2017 vol 11 No. 9 pp. 8777-8780.
Lee et al., "PEGylation to Improve Protein Stability During Melt Processing", Macromol Biosci 1-43, 57-75, Oct. 2015 vol 15 No. 10 pp. 1332-1337.
Lee, K. L., et al.; "Combination of Plant Virus Nanoparticle-Based in Situ Vaccination with Chemotherapy Potentiates Antitumor Response". Nano letters, 17(7); Epub Jun. 26, 2017; 4019-4028. https://doi.org/10.1021/acs.nanolett.7b00107.
Mitoxantrone. Drug Bank Online. Website. https://go.drugbank.com/drugs/DB01204. (Accessed Dec. 15, 2022) (Year: 2022).
Mosquera et al. (Acc. Chem. Res. 2018, 51, 9, 2305-2313 Publication Date: Aug. 29, 2018.
Nicole F. Steinmetz, U.S. Appl. No. 16/998,210, filed Aug. 7, 2020; Non-Final OA dated Dec. 7, 2022.
Nicole F. Steinmetz; U.S. Appl. No. 16/347,503, filed: May 3, 2019; NonFinal Rejection dated Jun. 15, 2022; 36 pgs.
Nicole F.Steinmetz, et al.; "Coated Plant Virus Imaging Agents"; U.S. Appl. No. 16/279,482, filed Feb. 19, 2019; Non-Final Rejection dated Mar. 23, 2021; 91 pgs.
Nicole F.Steinmetz; "Viral Nanoparticle Multimers"; U.S. Appl. No. 14/761,444, filed Jul. 16, 2015; Final Office Action dated Mar. 11, 2021; 11 pgs.
Nicole F.Steinmetz; U.S. Appl. No. 16/597,509, filed Oct. 9, 2019; Non-Final Office Action, dated Dec. 27, 2022; 12 pgs.
Nicole F.Steinmetz; U.S. Appl. No. 16/759,652, filed Apr. 27, 2020; Final Office Action, dated Dec. 12, 2022; 15 pgs.
Nicole F.Steinmetz; U.S. Appl. No. 17/129,463, filed Dec. 21, 2020; Non-Final Office Action, dated Dec. 8, 2022; 32 pgs.
Nicole F.Steinmetz; U.S. Appl. No. 17/522,182, filed Nov. 9, 2021; Non-Final Office Action, dated Jan. 5, 2023; 27 pgs.
Nicole F.Steinmetz; U.S. Appl. No. 17/677,147, filed Feb. 22, 2022; Non-Final Office Action, dated Jan. 13, 2023; 22 pgs.
Patrick h. lizotte: "Novel approaches to targeting innate immunity for cancer immunotherapy", Proquest Dissertations Publishing, May 2015 (May 2015), XP002780316, Retrieved from the Internet: URL:https://search.proquest.com/docview/1695832154?pq-origsite=gscholar [retrieved on Apr. 19, 2018].
Pellico et al. (Contrast Media and Molecular Imaging. 2019; Article ID 1845637: 1-13).
Pretto et al. ("Versatile reversible cross-linking strategy to stabilize CCMV virus like particles for efficient siRNA delivery." Bioconjugate chemistry 30.12 (2019): 3069-3077).
Royston et al. (Journal of Colloidal and Interface Science. 2009; 332: 402-407).
Saunders K et Al: "Efficient generation of cowpea mosaicvirus empty virus-like particles by the proteolytic processing of precursors in insect cells and plants", Virology, Elsevier, Amsterdam, NL, vol. 393, No. 2, Oct. 25, 2009 (Oct. 25, 2009), pp. 329-337, XP026691170, ISSN: 0042-6822, DOI: 10.1016/J.VIROL.2009.08.023 [retrieved on Sep. 5, 2009].
Tamoxifen. Drug Bank Online. Website. https://go.drugbank.com/drugs/DB00675. (Accessed: Dec. 15, 2022) (Year: 2022).
Temming et al. (bioconjugate Chemistry. 2006; 17: 1385-1394).
Tran, Hong Hanh. Developing a plant virus-based expression system for the expression of vaccines against Porcine Reproductive and Respiratory Syndrome Virus. Western Graduate & Postdoctoral Studies. Electronic Thesis and Dissertation Repository. (Year: 2017).
Xiao et al. (International Journal of Molecular Medicine. 2016; 38: 1319-326).
Zhang et al. (Theranostics. 2018; 8 (9): 2521-2548).
Wen et al. Design of virus-based nanomaterials for medicine, biotechnology, and energy. Chem. Soc. Rev., 2016, 45, 4074. DOI: 10.1039/c5cs00287g (Year: 2016).
Matsuura et al. Self-assembly of Ni-NTA-modified β-annulus peptides into artificial viral capsids and encapsulation of His-tagged proteins. Org. Biomol. Chem., 2016, 14, 7869. DOI: 10.1039/c6ob01227b (Year: 2016).

* cited by examiner

ANTICANCER TRAIL-TARGETED PLANT VIRUS PARTICLES

RELATED APPLICATION

This application claims priority to 62/507,603, filed May 17, 2017, the subject matter of which is incorporated herein by reference in its entirety.

BACKGROUND

Tumor necrosis factor-related apoptosis-inducing ligand (TRAIL), also known as Apo2L, is an innate immune cytokine broadly expressed by activated immune cells responsible for suppressing tumor initiation and metastasis. The protein specifically binds to death receptors, namely DR4 and DR5, which are overexpressed in many cancer cells but not healthy cells. TRAIL-DR4/5 interations launch a signaling cascade triggersing a caspase-dependent apoptosis process. This specificity makes TRAIL an attractive target for cancer therapy by restoring endogenous death pathways and thus driving cancer cells into self-destruction.

Similar to most TNF-ligands, TRAIL is expressed as a homotrimeric type II transmembrane protein or converted into a soluble form upon proteolytic cleavage. Since its discovery, TRAIL has been widely developed and tested as a therapeutic protein in oncology with promising results in various pre-clinical models. However, clinical trials with soluble TRAIL were disappointing, while TRAIL therapy demonstrated safety, lack of efficacy was attributed to the fact that soluble TRAIL has poor physiochemical properties and does not effectively trigger apoptosis in cancer cells. Therefore, a need remains for the development of delivery platforms to present multivalent TRAIL in a surface-bound state.

SUMMARY

Embodiments described herein relate to agents and there use in the treatment of cancer. The agents can include a plant virus particle or virus-like particle (VLP) conjugated to at least one tumor necrosis factor (TNF)-related apoptosis-inducing ligand (TRAIL). The plant virus particle or virus-like particle can include an icosahedral, filamentous, or rod shaped plant virus particle or VLP. The plant virus particle or VLP can be PEGylated.

In some embodiments, the filamentous plant virus particle or VLP can belong to the Alphaflexiviridae family. The filamentous plant virus particle or VLP can include a potato virus X (PVX). PVX can be non-covalently conjugated to TRAIL by coordination bonds between nickel-coordinated nitrilotriacetic acid (Ni-NTA) modules displayed on PVX surface and a His-tag on TRAIL.

In other embodiments, the rod shaped plant virus particle or VLP can include a tobacco mosaic virus (TMV).

In some embodiments, the plant virus particle or VLP can be loaded with or conjugated to one or more of an imaging agent, an anticancer agent, or a targeting agent. A targeting agent can include a ligand for a tumor-associated receptor, such as an EGFR ligand. An anticancer agent can include a platinum-based anticancer agent, such as phenanthriplatin, or doxorubicin. An imaging agent can include a fluorescent molecule for fluorescent imaging.

Other embodiments described herein also relate to methods of treating cancer in a subject. The method includes administering to the subject a therapeutically effective amount of an agent that includes a plant virus particle or virus-like particle (VLP) conjugated to at least one tumor necrosis factor (TNF)-related apoptosis-inducing ligand (TRAIL). In some embodiments, the therapeutically effective amount of the agent is an amount required to activate caspase-dependent apoptosis via TRAIL-DR4/5 receptor binding in cancer cells of the subject.

In some embodiments, the agent can be administered to the subject together with a pharmaceutically acceptable carrier. The plant virus particle or virus-like particle can include an icosahedral, filamentous, or rod shaped plant virus particle or virus-like particle. The plant virus particle or VLP can be PEGylated.

In some embodiments, the filamentous plant virus particle or VLP can belong to the Alphaflexiviridae family. The filamentous plant virus particle or VLP can include a potato virus X (PVX). PVX can be non-covalently conjugated to TRAIL by coordination bonds between nickel-coordinated nitrilotriacetic acid (Ni-NTA) modules displayed on PVX surface and a His-tag on TRAIL.

In other embodiments, the rod shaped plant virus particle or VLP can include a tobacco mosaic virus (TMV).

The plant virus particle or VLP can be loaded with or conjugated to one or more of an imaging agent, an anticancer agent, or a targeting agent. A targeting agent can include a ligand for a tumor-associated receptor, such as an EGFR ligand. An anticancer agent can include a platinum-based anticancer agent, such as phenanthriplatin, or doxorubicin. An imaging agent can include a fluorescent molecule for fluorescent imaging.

In some embodiments, where the plant virus particle or VLP is loaded with or conjugated to an imaging agent, the method further includes a step of imaging cancer tissue in the subject using an imaging device subsequent to administering the agent.

The cancer treated can be selected from the group consisting of breast cancer, ovarian cancer, soft-tissue sarcoma, pancreatic cancer, colorectal cancer, non-small cell lung cancer, lymphoma, non-Hodgkins lymphoma, and hepatocarcinoma. In certain embodiments, the cancer treated includes triple negative breast cancer.

For standard curves, HisTRAIL was loaded at 0.25, 0.5, 1, 2.5, and 5 μg (5-9), PVX was loaded at 0.1, 0.25, 0.5, 1 μg (5'-9'). Fluorescence intensities were read from FluoroChem instrument.

FIGS. 2(A-B) graphically illustrate (A) MTT cell viability assays of HisTRAIL vs. PVX-HisTRAIL in MDAMB-231 triple negative breast cancer cell line determined by MTT assay. (B) Levels of activated caspase-8 and caspase-3/7 after 3 h treatment by HisTRAIL or PVXHisTRAIL (20 ng/mL). Data were expressed as means±SD.

FIGS. 3(A-C) are graphs and images illustrating treatment of MDA-MB-231 xenografts in an athymic nude mouse model. 6-week-old female NCR nu/nu mice were injected subcutaneously into the right flank with $2 \times 10^6$ cells; treatment began when tumor volume reached 100-150 mm$^3$, approximately 2 weeks after tumor cell inoculation. Mice were assigned randomly to each group: PVX-HisTRAIL: n=6, HisTRAIL: n=5, PVX-Ni: n=4, and PBS: n=4. PVX-HisTRAIL or HisTRAIL was injected intratumorally at the dose of 5 μg protein/injection every other day. 20 μL PBS or corresponding particle amount of PVXNi were injected as controls. Tumor volume was normalized at the initial day. Data were expressed as expressed as means+SD. (A) Tumor growth curve during treatment. (B) Tumor volume distribution in each group during treatment. (C) Representative of isolated tumor tissues after treatment.

Figure 4:
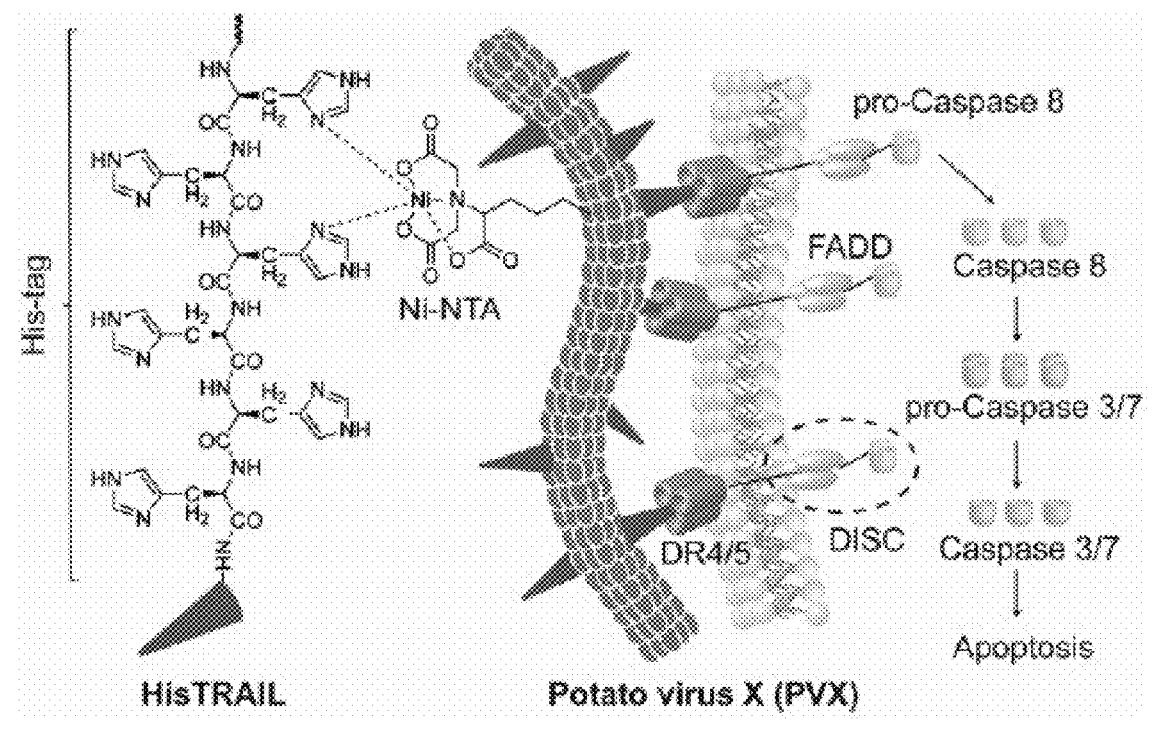

FIG. 4 is an illustration of the preparation of the therapeutic conjugate, PVX-HisTRAIL via the coordination bond between a Ni-NTA group on PVX and a His-tag at the N-terminus of HisTRAIL. Multivalent display of HisTRAIL on the elongated PVX particle allows efficient binding on death receptors DR4/5 to activate the caspase-dependent apoptosis in cancer cells.

Figure 5:
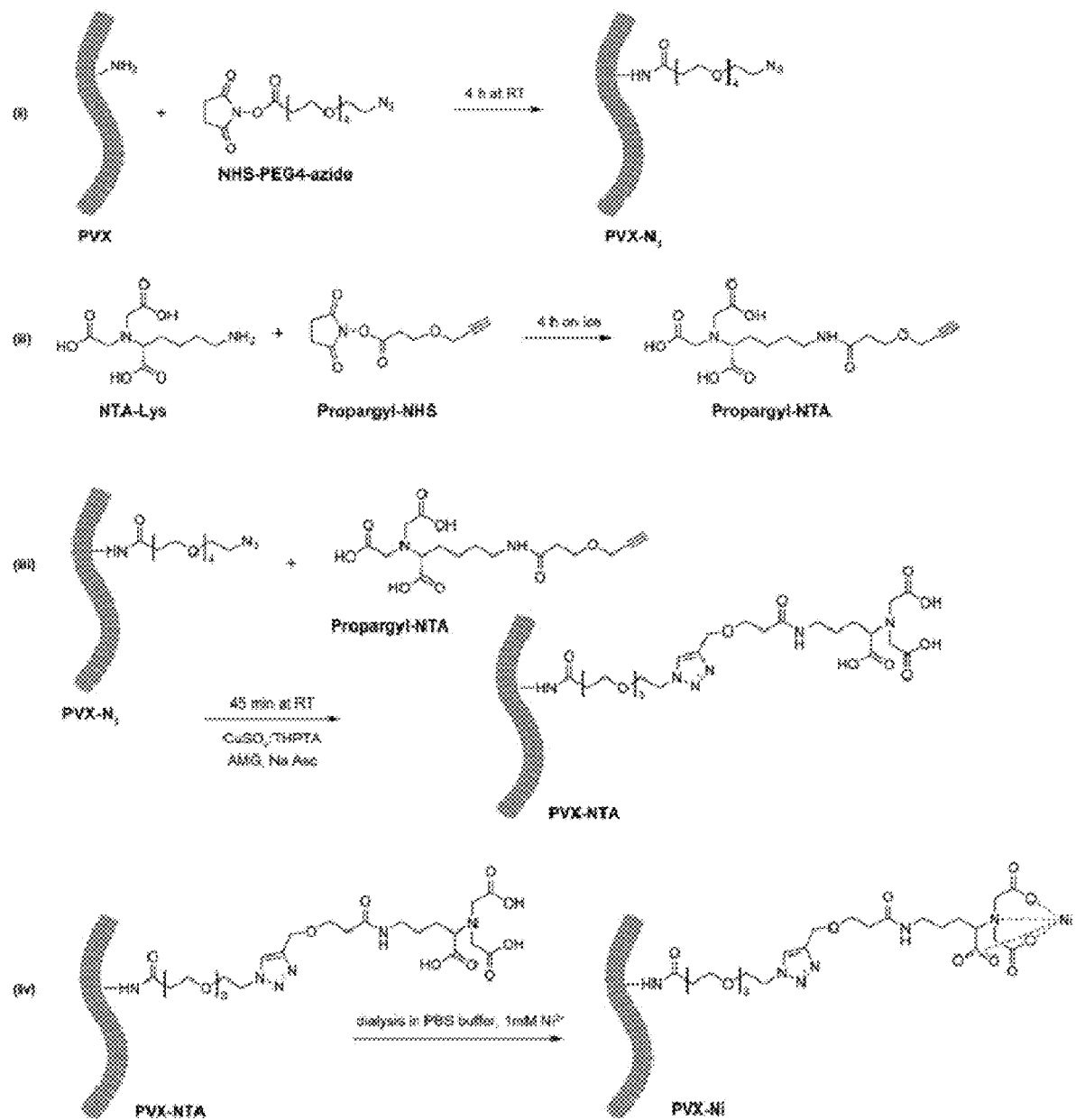

FIG. 5 illustrates a reaction scheme for synthesis of PVX displaying nickel-coordinated nitrilotriacetic acid, denoted PVX-Ni.

FIGS. 6(A-B) illustrates A) Schematic of the constructed pET-28a(+)/HisTRAIL plasmid encoding the bioactive domain of human TRAIL (aa 114-281) inserted at the corrresponding NdeI and SacI restriction enzyme sites, next to the N-terminal His-tag and thrombin cleavage tag from the orginial pET28a(+) plasmid. B) Denaturing gel electrophoresis (SDS-PAGE) and western blot analysis of purified HisTRAIL.

Figure 7A:
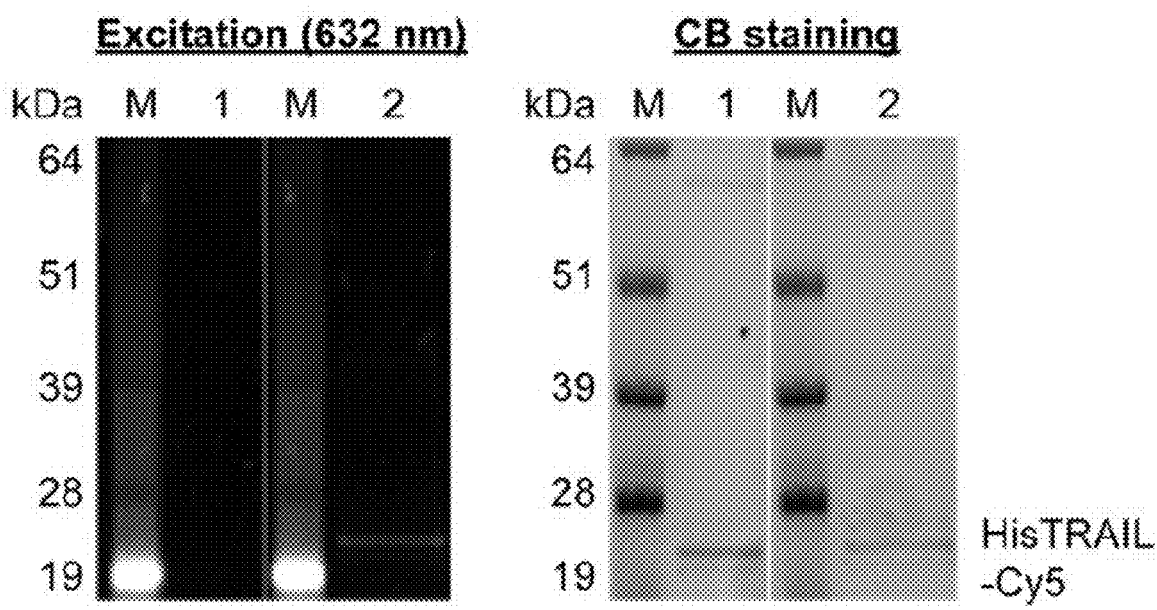
Figure 7B:
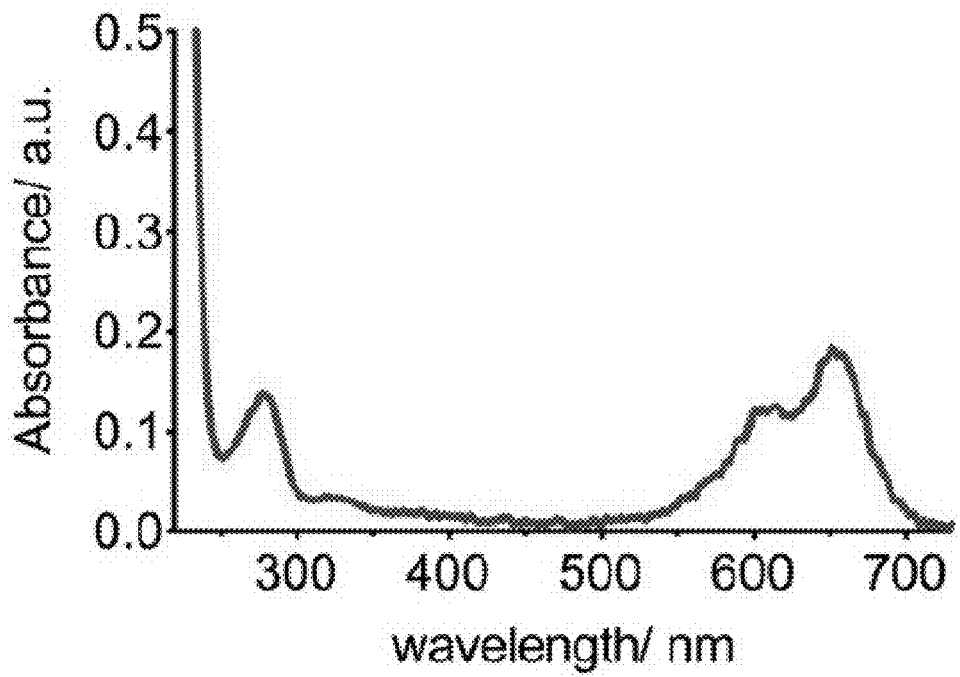

FIG. 7 illustrates (A) SDS-PAGE gel analysis of (1) unlabeled HisTRAIL vs. (2) fluorescently labeled HisTRAIL-Cy5 upon excitation at 632 nm and after CB staining. (B) The UV/Visible spectrum of HisTRAIL-Cy5.

Figure 8:
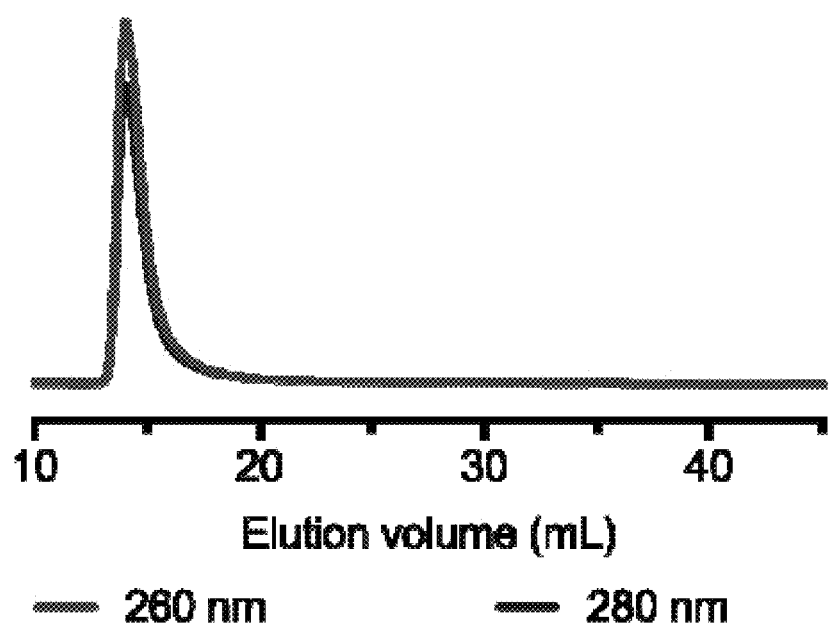

FIG. 8 illustrates the SEC profile of native PVX particle eluting from a Superose column. Native PVX elutes at 14.5 mL and the 260:280 nm ratio is determined.

Figure 9:
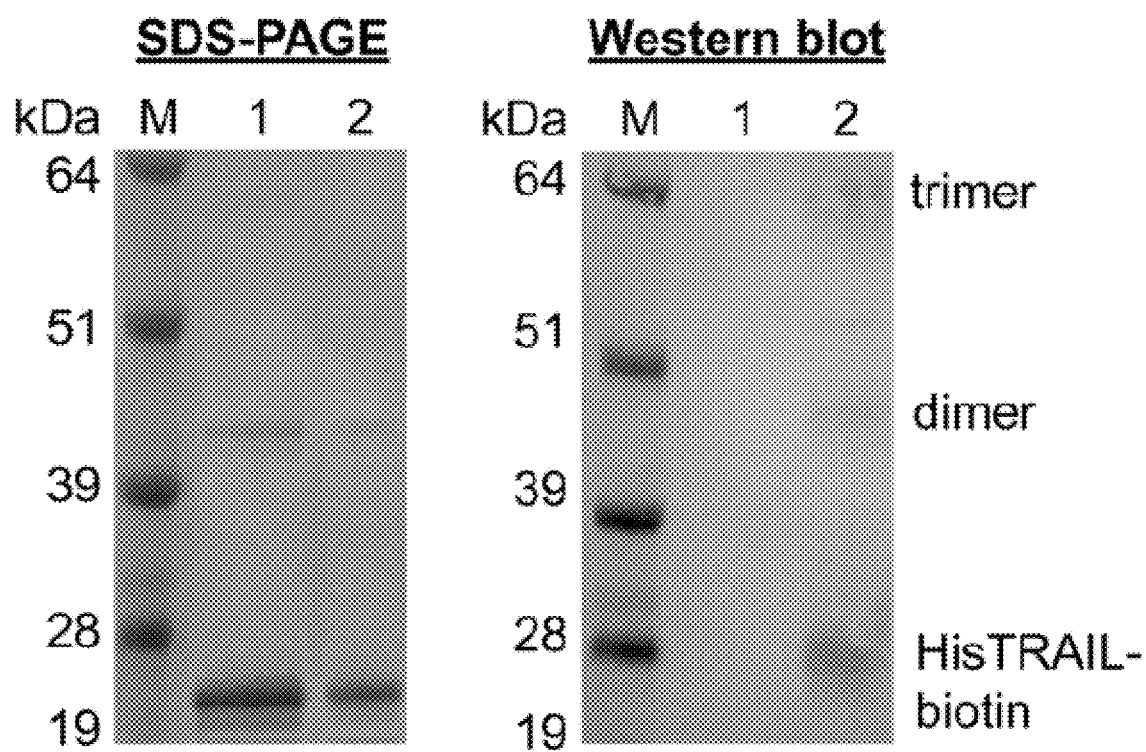

FIG. 9 illustrates results from SDS-PAGE and western blot analysis of (1) unlabeled HisTRAIL vs. (2) HisTRAIL-biotin.

Figure 10:
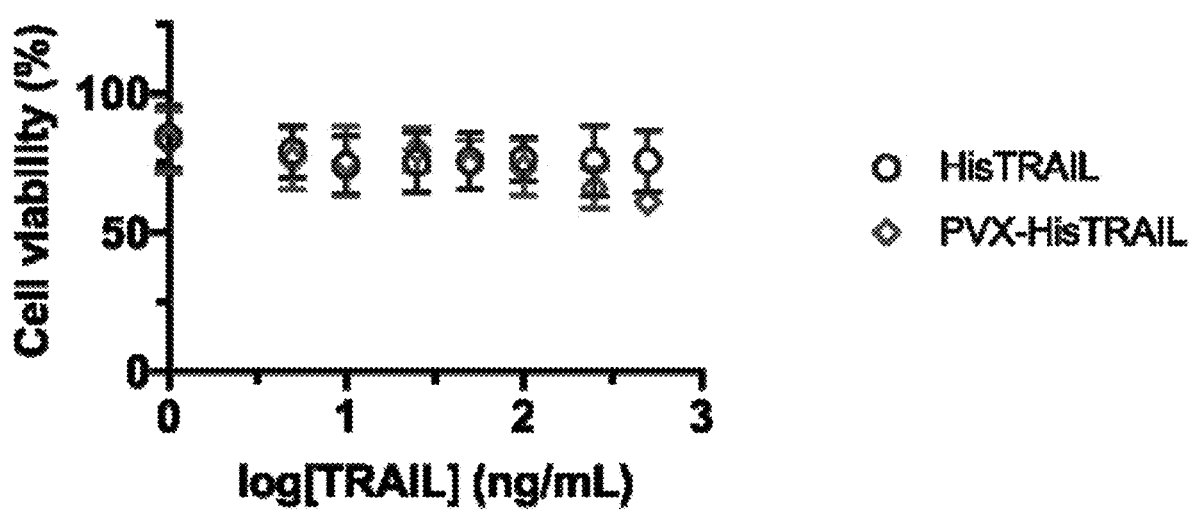

FIG. 10 illustrates illustrates in vitro efficacy of HisTRAIL vs. PVX-HisTRAIL in SK-BR-3, a HER2-amplified breast cancer cell line determined by MTT assay. Either PVX-HisTRAIL or HisTRAIL did not show cell killing efficacy in this cell line, consistent with previously reported data. Data are expressed as means±SD.

DETAILED DESCRIPTION

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the application pertains. Commonly understood definitions of molecular biology terms can be found in, for example, Rieger et al., *Glossary of Genetics: Classical and Molecular,* 5th Edition, Springer-Verlag: New York, 1991, and Lewin, *Genes V,* Oxford University Press: New York, 1994.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, and other references mentioned herein are incorporated by reference in their entirety.

Definitions

As used in this specification and the appended claims, the singular forms "a", "an" and "the" include plural references unless the content clearly dictates otherwise. Thus, for example, reference to "a cell" includes a combination of two or more cells, and the like. In addition, the recitations of numerical ranges by endpoints include all numbers subsumed within that range (e.g., 1 to 5 includes 1, 1.5, 2, 2.75, 3, 3.80, 4, 5, etc.).

The terms "comprise," "comprising,", "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably. Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "or" as used herein should be understood to mean "and/or", unless the context clearly indicates otherwise.

The term "about" as used herein when referring to a measurable value such as an amount, a temporal duration, and the like, is meant to encompass variations of ±20% or 110%, more preferably ±5%, even more preferably ±1%, and still more preferably ±0.1% from the specified value, as such variations are appropriate to perform the disclosed methods.

"Image" or "imaging" refers to a procedure that produces a picture of an area of the body, for example, organs, bones, tissues, or blood.

"Treat", "treating", and "treatment", etc., as used herein, refer to any action providing a benefit to a subject afflicted with a condition or disease such as cancer, including improvement in the condition through lessening or suppression of at least one symptom, delay in progression of the disease, etc.

A "prophylactic" or "preventive" treatment is a treatment administered to a subject who does not exhibit signs of a disease or disorder, or exhibits only early signs of the disease or disorder, for the purpose of decreasing the risk of developing pathology associated with the disease or disorder. The subject may be at risk due to exposure to a carcinogen, or as a result of family history.

The terms "cancer" or "tumor" refer to any neoplastic growth in a subject, including an initial tumor and any metastases. The cancer can be of the liquid or solid tumor type. Liquid tumors include tumors of hematological origin, including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkin's lymphoma). Solid tumors can originate in organs and include cancers of the lungs, brain, breasts, prostate, ovaries, colon, kidneys and liver.

The terms "cancer cell" or "tumor cell" can refer to cells that divide at an abnormal (i.e., increased) rate. Cancer cells include, but are not limited to, carcinomas, such as squamous cell carcinoma, non-small cell carcinoma (e.g., non-small cell lung carcinoma), small cell carcinoma (e.g., small cell lung carcinoma), basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; hematologic cancers, such as myelomas, leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkin's disease), and tumors of the nervous system including glioma, glioblastoma multiform, meningoma, medulloblastoma, schwannoma and epidymoma.

The term "nanoparticle" refers to any particle having a diameter of less than 1000 nanometers (nm). In general, the nanoparticles should have dimensions small enough to allow their uptake by eukaryotic cells. Typically the nanoparticles have a longest straight dimension (e.g., diameter) of 200 nm or less. In some embodiments, the nanoparticles have a diameter of 100 nm or less. Smaller nanoparticles, e.g., having diameters of 50 nm or less, e.g., about 1 nm to about 30 nm or about 1 nm to about 5 nm, are used in some embodiments.

The phrases "parenteral administration" and "administered parenterally" are art-recognized terms and include modes of administration other than enteral and topical administration, such as injections, and include, without limitation, intratumoral, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion. In certain embodiments, the targeted plant virus particle is intratumorally administered.

The phrases "systemic administration," "administered systemically," "peripheral administration" and "administered peripherally" as used herein mean the administration of a compound, agent or other material other than directly into a specific tissue, organ, or region of the subject being treated (e.g., tumor site), such that it enters the animal's system and, thus, is subject to metabolism and other like processes, for example, subcutaneous administration. IN certain embodiments, the targeted plant virus particle is systemically administered.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

"Pharmaceutically acceptable" as used herein means that the compound or composition is suitable for administration to a subject for the methods described herein, without unduly deleterious side effects in light of the severity of the disease and necessity of the treatment.

The language "effective amount" or "therapeutically effective amount" refers to a nontoxic but sufficient amount of the composition used in the practice of the invention that is effective to provide effective imaging or treatment in a subject, depending on the compound being used. That result can be reduction and/or alleviation of the signs, symptoms, or causes of a disease or disorder, or any other desired alteration of a biological system. An appropriate therapeutic amount in any individual case may be determined by one of ordinary skill in the art using routine experimentation.

A "therapeutic" treatment is a treatment administered to a subject who exhibits signs of pathology of a disease or disorder for the purpose of diminishing or eliminating those signs.

"Pharmaceutically acceptable carrier" refers herein to a composition suitable for delivering an active pharmaceutical ingredient, such as the composition of the present invention, to a subject without excessive toxicity or other complications while maintaining the biological activity of the active pharmaceutical ingredient. Protein-stabilizing excipients, such as mannitol, sucrose, polysorbate-80 and phosphate buffers, are typically found in such carriers, although the carriers should not be construed as being limited only to these compounds.

As used herein, the terms "peptide," "polypeptide" and "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof. A protein may be a receptor or a non-receptor.

A "nucleic acid" refers to a polynucleotide and includes polyribonucleotides and polydeoxyribonucleotides.

The term "antibody" as used herein refers to an immunoglobulin, whether natural or partly or wholly synthetically produced. The term also covers any polypeptide, protein or peptide having a binding domain that is, or is homologous to, an antibody binding domain. These can be isolated from natural sources, or may be partly or wholly synthetically produced. Examples of antibodies are intact immunoglobulin molecules, as well as to fragments thereof, such as Fab, F(ab')$_2$, Fv fragments, and single chain variable fragments (scFv), which are capable of binding an epitopic determinant. Antibody fragments refer to antigen-binding immunoglobulin peptides that are at least about 5 to about 15 amino acids or more in length, and that retain some biological activity or immunological activity of an immunoglobulin. Antibody as used herein includes polyclonal and monoclonal antibodies, hybrid, single chain, and humanized antibodies, as well as Fab fragments, including the products of a Fab or other immunoglobulin expression library, and suitable derivatives.

As used herein, a protein such as an antibody "specifically binds" when the antibody preferentially binds a target structure, or subunit thereof, but binds to a substantially lesser degree or does not bind to a biological molecule that is not a target structure. Antibodies that specifically bind to a target structure, or subunit thereof, do not cross-react with biological molecules that are outside the target structure family.

"Targeting," as used herein, refers to the ability of targeted viral particle to be delivered to and preferentially accumulate in cancer tissue in a subject.

As used herein, the term "targeting agent" can refer to a molecule or molecules that are able to bind to and complex with a biomarker. The term can also refer to a functional group that serves to target or direct a nanoparticle, therapeutic agent or anti-cancer agent to a particular location, cell type, diseased tissue, or association. In general, a "targeting agent" can be directed against a biomarker.

The present invention provides agents that include a plant virus particle or virus-like particle (VLP) conjugated to at least one tumor necrosis factor (TNF)-related apoptosis-inducing ligand (TRAIL). It was found that plant virus particles conjugated to TRAIL were effective to induce caspase-dependent apoptosis through DR4/5 receptor binding in cancer cells using a MTT cell viability assay and effective for inhibiting tumor growth in an ex vivo mouse model. Associating a death receptor-specific ligand, such as TRAIL, with a plant virus particle or VLP serves to both target cancer cells and induce their apoptosis. Without being bound by theory, conjugation of a plant virus particle or VLP to TRAIL allows for the TRAIL to mimic its membrane bound state and activate surface-overexpressed DR4/5 receptors on cancer cells thereby initiating caspase-dependent apoptosis in the cells. In some aspects, the targeted virus particles can therefore be used for a method of treating cancer in a subject.

TRAIL is a cytokine protein ligand that shows homology to other members of the tumor necrosis factor superfamily. TRAIL includes 281 amino acids and has characteristics of a type II transmembrane protein (i.e., no leader sequence and an internal transmembrane domain). TRAIL bind to death receptors DR4 (TRAIL-R1) and DR5 (TRAIL-R2). The TRAIL ligand conjugated to a plant virus particle or can include a bioactive fragment of a native human TRAIL protein capable of activating DR4 and/or DR5 death receptor of a cancer cell. For example, the TRAIL ligand can include an amino acid sequence corresponding to amino acid 114-281 of Human TRAIL. In some embodiments, the TRAIL ligand can be modified using well known methods to include an N-terminal His-Tag and/or a thrombin cleavage sequence allowing for removal of the His-tag if desired (See FIG. 6A).

Plant Virus Particles or VLPs

Plant virus particles preferably grow in plants, and have the advantages of being readily cultivated, and are unlikely to cause infection when used in vivo in a subject. In planta production prevents endotoxin contamination that may be a byproduct of other virus particle systems derived from *E. coli*. The plant virus particles or VLPs are scalable, stable over a range of temperatures (4-60° C.) and solvent:buffer mixtures.

In some embodiments, an agent includes a plant virus-like particles (VLPs) derived from an icosahedral, filamentous, or rod-shaped plant virus conjugated to at least one TRAIL ligand. VLPs are self-assembled structures derived from viral antigens that mimic the native architecture of viruses but lack the viral genome. VLPs lacking their nucleic acid are non-replicating and non-infectious regardless of the subject into which they are introduced.

In other embodiments, the plant virus particles include a nucleic acid within the virus particle. If present, the nucleic acid will typically be the nucleic acid encoding the virus. However, in some embodiments the viral nucleic acid may have been replaced with exogenous nucleic acid. In some embodiments, the nucleic acid is RNA, while in other embodiments the nucleic acid is DNA. A virus particle including nucleic acid will still be nonreplicating and non-infectious when it is introduced into a subject which it cannot infect. For example, plant virus particles will typically be nonreplicating and noninfectious when introduced into an animal subject.

Plant virus particles are categorized based on their source and structure. In various embodiments, virus particles having an icosahedral, filamentous, or rod-shaped structure can be used. Preferably, the plant virus particles used are non-enveloped virus particles. In certain embodiments, the use of filamentous or rod-shaped plant virus particles is preferred, in part as a result of the proclivity of these viral particles to be taken up by cancer cells. While not intending to be bound by theory, it appears that filamentous or rod-shaped plant virus particles are taken up by blood components such as macrophage cells of the immune system, which subsequently accumulate in tumor tissue.

In some embodiments, the plant virus particle or VLP is an icosahedral plant picornavirus or VLP. Plant picornaviruses are relatively small, non-enveloped, positive-stranded RNA viruses with an icosahedral capsid. Plant picornaviruses have a number of additional properties that distinguish them from other picornaviruses, and are categorized as the subfamily secoviridae. In some embodiments, the virus particles are selected from the Comovirinae virus subfamily. Examples of viruses from the Comovirinae subfamily include Cowpea mosaic virus (CPMV), Broad bean wilt virus 1, and Tobacco ringspot virus. In a further embodiment, the virus particles are from the Genus comovirus. A preferred example of a comovirus is CPMV.

In some embodiments, the plant virus or virus-like particle is a rod-shaped plant virus or VLP. A rod-shaped plant virus is a virus that primarily infects plants, is non-enveloped, and is shaped as a rigid helical rod with a helical symmetry. Rod shaped viruses also include a central canal.

Rod-shaped plant virus particles are distinguished from filamentous plant virus particles as a result of being inflexible, shorter, and thicker in diameter. For example, Virgaviridae have a length of about 200 to about 400 nm, and a diameter of about 15-25 nm. Virgaviridae have other characteristics, such as having a single-stranded RNA positive sense genome with a 3'-tRNA like structure and no polyA tail, and coat proteins of 19-24 kilodaltons.

In some embodiments, the rod-shaped plant virus or VLP belongs to a specific virus family, genus, or species. For example, in some embodiments, the rod-shaped plant virus belongs to the Virgaviridae family. The Virgaviridae family includes the genus Furovirus, Hordevirus, Pecluvirus, Pomovirus, Tobamovirus, and Tobravirus.

In some embodiments, the rod-shaped plant virus belongs to the genus Tobamovirus. In further embodiments, the rod-shaped plant virus belongs to the tobacco mosaic virus (TMV) species. The tobacco mosaic virus has a capsid made from 2130 molecules of coat protein and one molecule of genomic single strand RNA 6400 bases long. The coat protein self-assembles into the rod like helical structure (16.3 proteins per helix turn) around the RNA which forms a hairpin loop structure. The protein monomer consists of 158 amino acids which are assembled into four main alpha-helices, which are joined by a prominent loop proximal to the axis of the virion. Virions are ~300 nm in length and ~18 nm in diameter. Negatively stained electron microphotographs show a distinct inner channel of ~4 nm.

In further embodiments, the rod-shaped plant virus or virus-like particle can be combined with other rod-shaped plant virus particles by means of a thermal transition to form an RNA-free spherical nanoparticle (SNP). A SNP is a spherical arrangement of the coat proteins of a plurality of rod-shaped plant virus particles formed by thermal transition of the rod-shaped virus particles. SNPs can be labeled with suitable chemicals prior or post thermal transition; for example, NHS-based chemistries allow one to conjugate functional molecules to SNPs post thermal transition; the SNPs are stable and remain structurally sound after chemical modification. The SNPs can be formed from rod-shaped plant virus particles (e.g., TMV virus particles) by briefly heating the rod-shaped plant virus particles. For example, the rod-shaped plant virus particles can be induced to undergo a thermal transition into SNPs by heating at about 96° C. for about 10 to about 20 seconds. The SNPs are formed from the coat proteins of one or more individual rod-shaped plant virus particles. In various embodiments, the SNP can be formed from about 1 to 10 virus particles, from about 10 to about 20 virus particles, from about 20 to about 30 virus particles, from about 30 to about 40 virus particles, or from about 40 to about 50 virus particles. Depending on the nature of the coat proteins, the number of virus particles incorporated, and the virus particle concentration in the solution in which the thermal transition occurs, the spherical nanoparticles can also vary in size. In some embodiments, the SNPs have a size from about 50 nm to about 800 nm. In further embodiments, the SNPs have a size from about 100 to about 300 nm, or from about 150 to about 200 nm.

In some embodiments, the plant virus or virus-like particle is a filamentous plant virus or VLP. A filamentous plant virus is a virus that primarily infects plants and has a non-enveloped filamentous structure. A filamentous structure is a long, thin virion that has a filament-like or rod-like shape that is much longer than it is wide and therefore has a high-aspect ratio. For example, Alphaflexiviridae have a length of about 470 to about 800 nm, and a diameter of about 12-13 nm. Filament-like virus particles are flexible in addition to being long and thin, and therefore some embodiments of the invention are directed to use of a flexible filamentous plant virus. As described herein, use of filamentous plant viruses provides the advantages of improved tumor targeting and penetration. Embodiments of the invention can deliver about 10%, about 20%, about 30%, about 40%, or even about 50% or more of the injected dose to tumor tissue.

In some embodiments, the filamentous plant virus belongs to a specific virus family, genus, or species. For example, in some embodiments, the filamentous plant virus belongs to the Alphaflexiviridae family. The Alphaflexiviridae family of plant viruses typically have a length of about 470 to about 800 nm, and a diameter of about 12-13 nm. The Alphaflexiviridae family includes the genus Allexivirus, Botrexvirus, Lolavirus, Mandarivirus, Potexvirus, and Sclerodarnavirus. In some embodiments, the filamentous plant virus belongs to the genus Potexvirus. Examples of Potexvirus include Allium virus X, Alstroemeria virus X, Alternanthera mosaic virus, Asparagus virus 3, Bamboo mosaic virus, Cactus virus X, Cassava common mosaic virus, Cassava virus X, Clover yellow mosaic virus, Commelina virus X, Cymbidium mosaic virus, Daphne virus X, Foxtail mosaic virus, Hosta virus X, Hydrangea ringspot virus, Lagenaria mild mosaic virus, Lettuce virus X, Lily virus X, Malva mosaic virus, Mint virus X, Narcissus mosaic virus, Nerine virus X, Opuntia virus X, Papaya mosaic virus, Pepino mosaic virus, Phaius virus X, Plantago asiatica mosaic virus, Plantago severe mottle virus, Plantain virus X, Potato aucuba mosaic virus, Potato virus X, Schlumbergera virus X, Strawberry mild yellow edge virus, Tamus red mosaic virus, Tulip virus X, White clover mosaic virus, and Zygocactus virus X. In certain embodiments, the filamentous plant virus belongs to the Potato Virus X (PVX) species.

The plant virus particle or VLPs can be obtained according to various methods known to those skilled in the art. In embodiments where plant virus particles are used, the virus particles can be obtained from the extract of a plant infected by the plant virus. For example, cowpea mosaic virus can be grown in black eyed pea plants, which can be infected within 10 days of sowing seeds. Plants can be infected by, for example, coating the leaves with a liquid containing the virus, and then rubbing the leaves, preferably in the presence of an abrasive powder which wounds the leaf surface to allow penetration of the leaf and infection of the plant. Within a week or two after infection, leaves are harvested and viral nanoparticles are extracted. In the case of cowpea mosaic virus, 100 mg of virus can be obtained from as few as 50 plants. Procedures for obtaining plant virus particles using extraction of an infected plant are known to those skilled in the art. See Wellink J., Meth Mol Biol, 8, 205-209 (1998). Procedures are also available for obtaining virus-like particles. Saunders et al., Virology, 393(2):329-37 (2009). The disclosures of both of these references are incorporated herein by reference.

Conjugation of TRAIL and Plant Virus Particle or VLP

The plant virus particle or VLP can be conjugated to TRAIL in a variety of ways. For example, a plant virus particle or VLP can be directly or indirectly conjugated to TRAIL. In some embodiments, the TRAIL ligand can be covalently or non-covalently linked to the outer surface of the plant virus particle or VLP. In other embodiments, TRAIL can be linked to the plant virus particle by forming a fusion protein, such as an N-terminal coat fusion protein.

In one example, PVX or a PVX VLP is non-covalently conjugated to TRAIL. For example PVX can be non-covalently conjugated to TRAIL by coordination bonds between nickel-coordinated nitrilotriacetic acid (Ni-NTA) modules displayed on PVX surface and His-tags on the TRAIL proteins to mimic the bioactive "membrane bound" state in native TRAIL (See FIG. 4). PVX has multiple surface-exposed lysine residues that can be targeted to display about 1000 to about 1500 small chemical modifiers (e.g., Ni-NTA) per particle. PVX can be first conjugated at its solvent-exposed lysine residues to display nitrilotriacetic acid (PVX-NTA) using click chemistry (See FIG. 5). The PVX-NTA suspension can then be dialyzed towards a buffer including 1 mM Ni2+ for Ni-NTA chelate formation on PVX where the resulting particle is referred to as PVX-Ni. Conjugation of PVX displaying Ni-NTA and His-tagged TRAIL is achieved by mixing the components in a buffer solution. Specific binding of TRAIL to PVX via a N-terminal His-Tag allows orientational control and for the bioactive TRAIL at the C-terminus to be solvent-exposed upon plant virus particle display, therefore mimicking its membrane-bound state when in contact with surface-overexpressed DR4/5 receptors on cancers cells. In an exemplary embodiment, the PVX particles and His-tagged TRAIL can be mixed at a 1:900 molar ratio for 2 hours at room temperature in PBS pH 7.4 and purified using ultracentrifugation.

In some embodiments, at least about 100, about 200, about 300, about 400 or more TRAIL ligand molecules can be conjugated to and therefore displayed on a plant virus particle. In an exemplary embodiment, about 490 molecules are displayed on a PVX plant virus particle. Once mixed and conjugated, the PVX-TRAIL suspension can be stored with no apparent aggregation for at least two weeks at 4° C. in aqueous buffer conditions.

Additional Agents

In some embodiments, the invention makes use of a plant virus particle that is further loaded with or conjugated to one or more imaging agents, therapeutic agents, and/or targeting agents. While the plant virus particles or VLPs already have anticancer activity as a result of conjugation to the TRAIL death receptor-specific ligand, other anticancer agents such as cytotoxic compounds can be included to increase the antitumor activity, other targeting agents can be included to enhance the delivery and/or antitumor activity the particles to a targeted site, and/or other imaging agents can be included to track the particles and image the tumor being treated. In one embodiment, multiple molecules of a therapeutic agent, an imaging agent, or a targeting agent are loaded in or conjugated to plant virus particle or VLP. In another embodiment, more than one type of an imaging agent, anticancer agent, or a targeting agent can be loaded in or conjugated to a plant virus particle or VLP.

In general, imaging agents, anticancer agents, and/or targeting agents can be loaded in or conjugated to the targeted viral particle by any suitable technique, with appropriate consideration of the need for pharmacokinetic stability and reduced overall toxicity to the patient.

In some embodiments, imaging agents, anticancer agents, and/or targeting agents can be conjugated to a plant virus particle or VLP either directly or indirectly (e.g. via a linker group). In some embodiments, the agent is directly attached to a functional group capable of reacting with the agent. For example, plant viral coat proteins include lysines that have a free amino group that can be capable of reacting with a carbonyl-containing group, such as an anhydride or an acid halide, or with an alkyl group containing a good leaving group (e.g., a halide). Viral coat proteins also contain glutamic and aspartic acids. The carboxylate groups of these amino acids also present attractive targets for functionalization using carbodiimide activated linker molecules; cysteines can also be present which facilitate chemical coupling via thiol-selective chemistry (e.g., maleimide-activated compounds). In addition, genetic modification can be applied to introduce any desired functional residue, including non-natural amino acids, e.g. alkyne- or azide-functional groups. See Pokorski, J. K. and N. F. Steinmetz Mol Pharm 8(1): 29-43 (2011).

Alternatively, a suitable chemical linker group can be used. A linker group can serve to increase the chemical reactivity of a substituent on either the imaging agent, anticancer agent, and/or targeting agent or the plant virus particle or VLP, and thus increase the coupling efficiency. A preferred group suitable for attaching agents to the virus particle are lysine residues present in the viral coat protein. Suitable linkage chemistries include maleimidyl linkers and alkyl halide linkers and succinimidyl (e.g., N-hydroxysuccinimidyl (NHS)) linkers (which react with a primary amine on the filamentous plant virus particle). Several primary amine and sulfhydryl groups are present on viral coat proteins, and additional groups can be designed into recombinant viral coat proteins. It will be evident to those skilled in the art that a variety of bifunctional or polyfunctional reagents, both homo- and hetero-functional (such as those described in the catalog of the Pierce Chemical Co., Rockford, Ill.), can be employed as a linker group. Coupling can be effected, for example, through amino groups, carboxyl groups, sulfhydryl groups or oxidized carbohydrate residues.

Other types of linking chemistries are also available. For example, methods for conjugating polysaccharides to peptides are exemplified by, but not limited to coupling via alpha- or epsilon-amino groups to NaIO$_4$-activated oligosaccharide (Bocher et al., J. Immunol. Methods 27, 191-202 (1997)), using squaric acid diester (1,2-diethoxycyclobutene-3,4-dione) as a coupling reagent (Tietze et al. Bioconjug Chem. 2:148-153 (1991)), coupling via a peptide linker wherein the polysaccharide has a reducing terminal and is free of carboxyl groups (U.S. Pat. No. 5,342,770), and coupling with a synthetic peptide carrier derived from human heat shock protein hsp65 (U.S. Pat. No. 5,736,146). Further methods for conjugating polysaccharides, proteins, and lipids to plant virus peptides are described by U.S. Pat. No. 7,666,624.

In some embodiments, for example where a anticancer agent is more potent when free from the plant virus particle of the present invention, it can be desirable to use a linker group which is cleavable during or upon internalization into a cancer cell, or which is gradually cleavable over time in the extracellular environment. A number of different cleavable linker groups have been described. The mechanisms for the intracellular release of a cytotoxic moiety agent from these linker groups include cleavage by reduction of a disulfide bond (e.g., U.S. Pat. No. 4,489,710); by irradiation of a photolabile bond (e.g., U.S. Pat. No. 4,625,014); by hydrolysis of derivatized amino acid side chains (e.g., U.S. Pat. No. 4,638,045); by serum complement-mediated hydrolysis (e.g., U.S. Pat. No. 4,671,958); and acid-catalyzed hydrolysis (e.g., U.S. Pat. No. 4,569,789).

It can be desirable to couple more than one imaging agent, anticancer agent, and/or targeting agent to a targeted viral particle of the invention. By poly-derivatizing the plant viral particle of the invention, several cytotoxic strategies can be simultaneously implemented. For example, a plant viral particle conjugated to TRAIL can be labeled for tracking by a visualization technique. In one embodiment, multiple molecules of a cytotoxic anticancer agent compound are coupled to a plant virus particle of VLP. In another embodiment, more than one type of cytotoxic compound can be coupled to a targeted viral particle.

In some embodiments, plant virus particles or VLPs can be functionalized by loading with or conjugated to an imaging agent, an anticancer agent and/or a targeting agent through the use of non-covalent infusion techniques that facilitate efficient cargo loading of one or more of an imaging agent, anticancer agent or a targeting agent into the plant virus particle or VLPs.

Anticancer Agents

In certain embodiments of the invention, the plant virus particle can be loaded with or conjugated to one or more anticancer agents. In some embodiments, the anticancer agent is a cytotoxic compound that inhibits cell growth or promotes cell death when proximate to or absorbed by a cell. Suitable cytotoxic compounds in this regard include radioactive agents or isotopes (radionuclides), chemotoxic agents such as differentiation inducers, inhibitors and small chemotoxic drugs, toxin proteins and derivatives thereof, as well as nucleotide sequences (or their antisense sequence). Therefore, the cytotoxic compound can be, by way of non-limiting example, an antitumor agent, a photoactivated toxin or a radioactive agent.

Preferred radionuclides for use as cytotoxic compounds are radionuclides which are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At can be conjugated to plant virus particles or VLPs utilizing any of several known conjugation reagents, including Iodogen, N-succinimidyl 3-[$^{211}$At]astatobenzoate, N-succinimidyl 3-[$^{131}$I]iodobenzoate (SIB), and, N-succinimidyl 5-[$^{131}$I]iodo-3-pyridinecarboxylate (SIPC). Any iodine isotope can be utilized in the recited iodo-reagents. Other radionuclides can be conjugated to the targeted viral particle by suitable chelation agents known to those of skill in the nuclear medicine arts.

Cytotoxic compounds include small-molecule antitumor agents. Examples of antitumor agents include angiogenesis inhibitors such as angiostatin K1-3, DL-α-difluoromethylornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, phenanthriplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives thereof. Antitumor agents can be directly conjugated to the plant virus particle or VLP via a chemical linker, or can be encapsulated in a carrier, which is in turn coupled to the plant virus particle or VLP.

In a particular embodiment, the plant virus particle or VLP conjugated to TRAIL can be further conjugated to or loaded with doxorubicin. For example the doxorubicin can be loaded within the groove of a PVX particle and utilized in the treatment of drug-resistant cancers.

In some embodiments, the anticancer agent is contained within the interior of the plant virus particle or VLP. Preferably, the anticancer agent is found solely in the interior, with little or no anticancer agent associating with the exterior of the plant virus particle or VLP. In some embodiments, the anticancer agent is a cationic anticancer agent that is non-covalently encapsulated in the interior of the plant virus particle, while in other embodiments the anticancer agent is covalently conjugated to the interior of the plant virus particle, using, for example, a linking chemistry. Cationic anticancer agents can be readily identified by those skilled in the art. Cationic anticancer agents can be loaded into the plant virus particles using an electrostatically-driven process through interaction of the positively charged drug with the negatively-charged interior protein surface of the hollow virus structure. The anticancer agent can be associated with the interior of the virus particle either as a result for an affinity to an interior structure such as a channel within the interior of the plant virus particle or VLP, or by linkage through groups only expressed on the interior of the virus particle.

In further embodiments, the anticancer agent is a platinum-based anticancer agent. Platinum-based anticancer agents include both neutral (platinum(II)) and cationic (platinum(IV)) platinum-based anticancer agents. Examples of neutral platinum-based anticancer agents include cisplatin, carboplatin, oxaliplatin, nedaplatin, and lobaplatin, which are in a sense more traditional platinum-based anticancer compounds. Cationic platinum-based anticancer agents include a variety of compounds such as satraplatin, picoplatin, and phenanthriplatin. In certain embodiments, the cationic platinum-based anticancer agent is phenanthriplatin. For additional platinum(IV) anticancer agents, see Lovejoy, K, and Lippard, S., Dalton Trans. 48, 10651-10659 (2009) and Zheng et al., JACS, 136, 8790-8798 (2014), the disclosures of which are incorporated herein by reference.

Preferred toxin proteins for use as cytotoxic compounds include ricin, abrin, diphtheria toxin, cholera toxin, gelonin, *Pseudomonas* exotoxin, *Shigella* toxin, pokeweed antiviral protein, and other toxin proteins known in the medicinal biochemistry arts. As these toxin agents can elicit undesirable immune responses in the patient, especially if injected intravascularly, it is preferred that they be encapsulated in a carrier for coupling to the plant virus particle or VLP.

Targeting Agents

In certain embodiments of the invention, the plant virus particle or VLP can be loaded with or conjugated to one or more targeting agents that are capable of targeting and/or adhering the plant virus particle or VLP to a cell or tissue of interest (e.g., cancer cell or tumor). The targeting agent may be attached directly to the plant virus particle or VLP. In some embodiments, one or more targeting agents can be conjugated to the plant virus particle or VLP exterior surface to provide easier access to the target molecule.

In some embodiments, the targeting agent may be associated with or coupled to the plant virus particle or VLP using a linker. The linker can be of any suitable length and contain any suitable number of atoms and/or subunits. The linker can include one or combination of chemical and/or biological moieties. Examples of chemical moieties can include alkyl groups, methylene carbon chains, ether, polyether, alkyl amide linkers, alkenyl chains, alkynyl chains, disulfide groups, and polymers, such as poly(ethylene glycol) (PEG), functionalized PEG, PEG-chelant polymers, dendritic polymers, and combinations thereof. Examples of biological moieties can include peptides, modified peptides, streptavidin-biotin or avidin-biotin, polyaminoacids (e.g., polylysine), polysaccharides, glycosaminoglycans, oligonucleotides, phospholipid derivatives, and combinations thereof.

The targeting agent can comprise any molecule, or complex of molecules, which is/are capable of interacting with an intracellular, cell surface, or extracellular biomarker of the cell. The biomarker can include, for example, a cellular protease, a kinase, a protein, a cell surface receptor, a lipid, and/or fatty acid. Other examples of biomarkers that the targeting agent can interact with include molecules associated with a particular disease. For example, the biomarkers can include cell surface receptors implicated in cancer development, such as epidermal growth factor receptor and transferrin receptor, or cancer metastasis, such as $\alpha_v\beta_3$ integrin. The targeting moieties can interact with the biomarkers through, for example, non-covalent binding, covalent binding, hydrogen binding, van der Waals forces, ionic bonds, hydrophobic interactions, electrostatic interaction, and/or combinations thereof.

The targeting agents can include, but are not limited to, synthetic compounds, natural compounds or products, macromolecular entities, bioengineered molecules (e.g., polypeptides, lipids, polynucleotides, antibodies, antibody fragments), and small entities (e.g., small molecules, neurotransmitters, substrates, ligands, hormones and elemental compounds).

In one example, the targeting agent can include an antibody, such as a monoclonal antibody, a polyclonal antibody, or a humanized antibody. The antibody can include Fv fragments, single chain Fv (scFv) fragments, Fab' fragments, F(ab')2 fragments, single domain antibodies, camelized antibodies and other antibody fragments. The antibody can also include multivalent versions of the foregoing antibodies or fragments thereof including monospecific or bispecific antibodies, such as disulfide stabilized Fv fragments, scFv tandems ((scFv)$_2$ fragments), diabodies, tribodies or tetrabodies, which typically are covalently linked or otherwise stabilized (i.e., leucine zipper or helix stabilized) scFv fragments; and receptor molecules, which naturally interact with a desired target molecule.

In some embodiments, the antibody is directed against a cell-surface marker on a cancer cell; that is, the target molecule is a cell surface molecule. As is known in the art, there are a wide variety of antibodies known to be differentially expressed on tumor cells, including, but not limited to, HER2. Examples of physiologically relevant carbohydrates may be used as cell-surface markers include, but are not limited to, antibodies against markers for breast cancer (CA 15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

In some embodiments, the targeting agent can include an agonistic anti-human DR4/TRAIL-R1 and DR5/TRAIL-R2-specific mAb. Exemplary TRAIL receptor agonist mAbs include the anti-TRAIL-R1 antibody mapatumumab (HGS-ETR1), anti-TRAIL-R2 antibodies conatumumab (AMG 655), drozitumab, lexatumumab (HGS-ETR2), LBY135, and tigatuzumab (CS-1008). In certain embodiments, a plant virus particle described herein conjugated to one or more agonistic anti-human DR4/5 TRAIL receptor-specific mABs can be administered to a subject for the treatment of cancer in combination with one or more of the anticancer agents selected from the group consisting of gemcitabine, cisplatin, paclitaxil, carboplatin, FOLFOX6, bevacizumab, ganitumab (AMG 479), FOLFIRI, pemetrexed, doxorubicin, and capecitabine.

Preparation of antibodies can be accomplished by any number of methods for generating antibodies. These methods typically include the step of immunization of animals, such as mice or rabbits, with a desired immunogen (e.g., a desired target molecule or fragment thereof). Once the mammals have been immunized, and boosted one or more times with the desired immunogen(s), antibody-producing hybridomas may be prepared and screened according to well known methods. See, for example, Kuby, Janis, Immunology, Third Edition, pp. 131-139, W.H. Freeman & Co. (1997), for a general overview of monoclonal antibody production, that portion of which is incorporated herein by reference.

In vitro methods that combine antibody recognition and phage display techniques can also be used to allow one to amplify and select antibodies with very specific binding capabilities. See, for example, Holt, L. J. et al., "The Use of Recombinant Antibodies in Proteomics," Current Opinion in Biotechnology, 2000, 11:445-449, incorporated herein by reference. These methods typically are much less cumbersome than preparation of hybridomas by traditional monoclonal antibody preparation methods.

In some embodiments, phage display technology may be used to generate a targeting agent specific for a desired target molecule. An immune response to a selected immunogen is elicited in an animal (such as a mouse, rabbit, goat or other animal) and the response is boosted to expand the immunogen-specific B-cell population. Messenger RNA is isolated from those B-cells, or optionally a monoclonal or polyclonal hybridoma population. The mRNA is reverse-transcribed by known methods using either a poly-A primer or murine immunoglobulin-specific primer(s), typically specific to sequences adjacent to the desired $V_H$ and $V_L$ chains, to yield cDNA. The desired $V_H$ and $V_L$ chains are amplified by polymerase chain reaction (PCR) typically using $V_H$ and $V_L$ specific primer sets, and are ligated together, separated by a linker. $V_H$ and $V_L$ specific primer sets are commercially available, for instance from Stratagene, Inc. of La Jolla, Calif. Assembled $V_H$-linker-$V_L$ product (encoding a scFv fragment) is selected for and amplified by PCR. Restriction sites are introduced into the ends of the $V_H$-linker-$V_L$ product by PCR with primers including restriction sites and the scFv fragment is inserted into a suitable expression vector (typically a plasmid) for phage display. Other fragments, such as a Fab' fragment, may be cloned into phage display vectors for surface expression on phage particles. The phage may be any phage, such as lambda, but typically is a filamentous phage, such as Fd and M13, typically M13.

In phage display vectors, the $V_H$-linker-$V_L$ sequence is cloned into a phage surface protein (for M13, the surface proteins g3p (pIII) or g8p, most typically g3p). Phage display systems also include phagemid systems, which are based on a phagemid plasmid vector containing the phage surface protein genes (for example, g3p and g8p of M13) and the phage origin of replication. To produce phage particles, cells containing the phagemid are rescued with helper phage providing the remaining proteins needed for the generation of phage. Only the phagemid vector is packaged in the resulting phage particles because replication of the phagemid is grossly favored over replication of the helper phage DNA. Phagemid packaging systems for production of antibodies are commercially available. One example of a commercially available phagemid packaging system that also permits production of soluble ScFv fragments in bacterial cells is the Recombinant Phage Antibody System (RPAS), commercially available from Amersham Pharmacia Biotech, Inc. of Piscataway, N.J. and the pSKAN Phagemid Display System, commercially available from MoBiTec, LLC of Marco Island, Fla. Phage display systems, their construction, and screening methods are described in detail in, among others, U.S. Pat. Nos. 5,702,892, 5,750,373, 5,821,047 and 6,127,132, each of which is incorporated herein by reference in their entirety.

The targeting agent need not originate from a biological source. The targeting agent may, for example, be screened from a combinatorial library of synthetic peptides. One such method is described in U.S. Pat. No. 5,948,635, incorporated herein by reference, which described the production of phagemid libraries having random amino acid insertions in the pIII gene of M13. These phage may be clonally amplified by affinity selection as described above.

The immunogens used to prepare targeting moieties having a desired specificity will generally be the target molecule, or a fragment or derivative thereof. Such immunogens may be isolated from a source where they are naturally occurring or may be synthesized using methods known in the art. For example, peptide chains may be synthesized by 1-ethyl-3-[dimethylaminoproply]carbodiimide (EDC)-catalyzed condensation of amine and carboxyl groups. In certain embodiments, the immunogen may be linked to a carrier bead or protein. For example, the carrier may be a functionalized bead such as SASRIN resin commercially available from Bachem, King of Prussia, Pa. or a protein such as keyhole limpet hemocyanin (KLH) or bovine serum albumin (BSA). The immunogen may be attached directly to the carrier or may be associated with the carrier via a linker, such as a non-immunogenic synthetic linker (for example, a polyethylene glycol (PEG) residue, amino caproic acid or derivatives thereof) or a random, or semi-random polypeptide.

In certain embodiments, it may be desirable to mutate the binding region of the polypeptide targeting agent and select for a targeting agent with superior binding characteristics as compared to the un-mutated targeting agent. This may be accomplished by any standard mutagenesis technique, such as by PCR with Taq polymerase under conditions that cause errors. In such a case, the PCR primers could be used to amplify scFv-encoding sequences of phagemid plasmids under conditions that would cause mutations. The PCR product may then be cloned into a phagemid vector and screened for the desired specificity, as described above.

In other embodiments, the targeting agents may be modified to make them more resistant to cleavage by proteases. For example, the stability of targeting agent comprising a polypeptide may be increased by substituting one or more of the naturally occurring amino acids in the (L) configuration with D-amino acids. In various embodiments, at least 1%, 5%, 10%, 20%, 50%, 80%, 90% or 100% of the amino acid residues of targeting agent may be of the D configuration. The switch from L to D amino acids neutralizes the digestion capabilities of many of the ubiquitous peptidases found in the digestive tract. Alternatively, enhanced stability of a targeting agent comprising a peptide bond may be achieved by the introduction of modifications of the traditional peptide linkages. For example, the introduction of a cyclic ring within the polypeptide backbone may confer enhanced stability in order to circumvent the effect of many proteolytic enzymes known to digest polypeptides in the stomach or other digestive organs and in serum. In still other embodiments, enhanced stability of a targeting moiety may be achieved by intercalating one or more dextrorotatory amino acids (such as, dextrorotatory phenylalanine or dextrorotatory tryptophan) between the amino acids of targeting moiety. In exemplary embodiments, such modifications increase the protease resistance of a targeting agent without affecting the activity or specificity of the interaction with a desired target molecule.

In certain embodiments, a targeting agent as described herein may comprise a homing peptide, which selectively directs the agent including a plant virus particle conjugated to TRAIL to a targeted cell. Homing peptides for a targeted cell can be identified using various methods well known in the art. Many laboratories have identified the homing peptides that are selective for cells of the vasculature of brain, kidney, lung, skin, pancreas, intestine, uterus, adrenal gland, retina, muscle, prostate, or tumors. See, for example, Samoylova et al., 1999, Muscle Nerve, 22:460; Pasqualini et al., 1996 Nature, 380:364; Koivunen et al., 1995, Biotechnology, 13:265; Pasqualini et al., 1995, J. Cell Biol., 130: 1189; Pasqualini et al., 1996, Mole. Psych., 1:421, 423; Rajotte et al., 1998, J. Clin. Invest., 102:430; Rajotte et al., 1999, J. Biol. Chem., 274:11593. See, also, U.S. Pat. Nos. 5,622,699; 6,068,829; 6,174,687; 6,180,084; 6,232,287; 6,296,832; 6,303,573; and 6,306,365.

Phage display technology provides a means for expressing a diverse population of random or selectively randomized peptides. Various methods of phage display and methods for producing diverse populations of peptides are well known in the art. For example, methods for preparing diverse populations of binding domains on the surface of a phage have been described in U.S. Pat. No. 5,223,409. In particular, phage vectors useful for producing a phage display library as well as methods for selecting potential binding domains and producing randomly or selectively mutated binding domains are also provided in U.S. Pat. No. 5,223,409. Similarly, methods of producing phage peptide display libraries, including vectors and methods of diversifying the population of peptides that are expressed, are also described in Smith et al., 1993, Meth. Enzymol., 217:228-257, Scott et al., Science, 249:386-390, and two PCT publications WO 91/07141 and WO 91/07149. Phage display technology can be particularly powerful when used, for example, with a codon based mutagenesis method, which can be used to produce random peptides or randomly or desirably biased peptides (see, e.g., U.S. Pat. No. 5,264, 563). These or other well-known methods can be used to produce a phage display library, which can be subjected to the in vivo phage display method in order to identify a peptide that homes to one or a few selected tissues.

In vitro screening of phage libraries has previously been used to identify peptides that bind to antibodies or cell surface receptors (see, e.g., Smith, et al., 1993, Meth. Enzymol., 217:228-257). For example, in vitro screening of phage peptide display libraries has been used to identify novel peptides that specifically bind to integrin adhesion receptors (see, e.g., Koivunen et al., 1994, J. Cell Biol.

124:373-380), and to the human urokinase receptor (Goodson, et al., 1994, Proc. Natl. Acad. Sci., USA 91:7129-7133).

In certain embodiments, the targeting agent may comprise a receptor molecule, including, for example, receptors, which naturally recognize a specific desired molecule of a target cell. A wide variety of tumor-associated receptors are known to those skilled in the art. Examples of tumor-associated receptors include integrin receptors and epidermal growth factor receptors (EGFR). Such receptor molecules include receptors that have been modified to increase their specificity of interaction with a target molecule, receptors that have been modified to interact with a desired target molecule not naturally recognized by the receptor, and fragments of such receptors (see, e.g., Skerra, 2000, J. Molecular Recognition, 13:167-187). A preferred receptor is a chemokine receptor. Exemplary chemokine receptors have been described in, for example, Lapidot et al, 2002, Exp Hematol, 30:973-81 and Onuffer et al, 2002, Trends Pharmacol Sci, 23:459-67.

In some embodiments, the targeting agent can include cyclo (ARG-GLY-ASP-D-Phe-Cys) or (cRGDfC), which is a ligand for vascular targeting and metastasis. In some embodiments, a detergent compatible can be used to quantify the number of peptides per FeMSN particles.

In other embodiments, the targeting agent can be a targeting peptide comprising an epidermal growth factor (EGF peptide). The EGF peptide may comprise the amino acid sequence YHWYGYTPQNVI-amide. The peptide may be synthesized by any method known in the art. For example, the EGF peptide may be synthesized manually using Fmoc protected amino acids (Peptides International, Louisville, KY) on rink-amide CLEAR resin (Peptides International, Louisville, KY, 100-200 mesh size, 0.4 milliequivalents/gram).

In still other embodiments, the targeting agent may comprise a ligand molecule, including, for example, ligands which naturally recognize a specific desired receptor of a target cell, such as a Transferrin (Tf) ligand. Such ligand molecules include ligands that have been modified to increase their specificity of interaction with a target receptor, ligands that have been modified to interact with a desired receptor not naturally recognized by the ligand, and fragments of such ligands.

In other embodiments, the targeting agent may comprise an aptamer. Aptamers are oligonucleotides that are selected to bind specifically to a desired molecular structure of the target cell. Aptamers typically are the products of an affinity selection process similar to the affinity selection of phage display (also known as in vitro molecular evolution). The process involves performing several tandem iterations of affinity separation, e.g., using a solid support to which the diseased immunogen is bound, followed by polymerase chain reaction (PCR) to amplify nucleic acids that bound to the immunogens. Each round of affinity separation thus enriches the nucleic acid population for molecules that successfully bind the desired immunogen. In this manner, a random pool of nucleic acids may be "educated" to yield aptamers that specifically bind target molecules. Aptamers typically are RNA, but may be DNA or analogs or derivatives thereof, such as, without limitation, peptide nucleic acids (PNAs) and phosphorothioate nucleic acids.

In yet other embodiments, the targeting agent may be a peptidomimetic. By employing, for example, scanning mutagenesis to map the amino acid residues of a protein, which is involved in binding other proteins, peptidomimetic compounds can be generated which mimic those residues which facilitate the interaction. Such mimetics may then be used as a targeting agent to deliver the composition to a target cell. For instance, non-hydrolyzable peptide analogs of such resides can be generated using benzodiazepine (e.g., see Freidinger et al. in Peptides: Chemisty and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988), keto-methylene pseudopeptides (Ewenson et al., 1986, J Med Chem 29:295; and Ewenson et al., in Peptides: Structure and Function (Proceedings of the 9th American Peptide Symposium) Pierce Chemical Co. Rockland, Ill., 1985), b-turn dipeptide cores (Nagai et al., 1985, Tetrahedron Lett 26:647; and Sato et al., 1986, J Chem Soc Perkin Trans 1:1231), and β-aminoalcohols (Gordon et al., 1985, Biochem Biophys Res Cummun 126:419; and Dann et al., 1986, Biochem Biophys Res Commun 134:71).

In some embodiments, the plant virus particle or VLP can include multiple types of targeting agents and the spacing and location of the targeting moieties on each plant virus particle or VLP can be controlled to facilitate delivery, targeting, and/or therapeutic efficacy of the agent(s).

Imaging Agents

In some embodiments, the plant virus particle or VLP can be loaded with or conjugated to one or more imaging agents to track the particles and image the tumor being treated. Examples of imaging agents include fluorescent, radioactive isotopes, MRI contrast agents, enzymatic moieties, or detectable label. For example, in some embodiments, the imaging agent is a fluorescent molecule for fluorescent imaging. The detectable label can be any material having a detectable physical or chemical property. Such detectable labels have been well-developed in the field of fluorescent imaging, magnetic resonance imaging, positive emission tomography, or immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™), fluorescent dyes (e.g., fluorescein isothiocyanate, AlexaFluor555, Texas red, rhodamine, and the like), radiolabels (e.g., $^{3}H$, $^{14}C$, $^{35}S$, $^{125}I$, $^{112}In$, $^{99}mTc$), other imaging agents such as microbubbles (for ultrasound imaging), $^{18}F$, $^{11}C$, $^{15}O$, (for Positron emission tomography), $^{99}mTC$, $^{111}In$ (for Single photon emission tomography), gadolinium chelate or iron (for magnetic resonance imaging), enzymes (e.g., horse radish peroxidase, alkaline phosphatase and others commonly used in an ELISA), and calorimetric labels such as colloidal gold or colored glass or plastic (e.g. polystyrene, polypropylene, latex, and the like) beads.

In some embodiments, the detectable moiety includes a fluorescent dye. Exemplary Fluorescent dyes include fluorescein isothiocyanate, cyanines such as Cy5, Cy5.5 and analogs thereof (e.g., sulfo-Cyanine 5 NHS ester and Cy5.5 maleimide). In a particular embodiment, TRAIL is labeled with Cy5 fluorescent dye (See FIG. 8). See also Handbook of Fluorescent Probes and Research Chemicals, 6$^{th}$ Ed., Molecular Probes, Inc., Eugene Oreg, which is incorporated herein by reference.

The label may be coupled directly or indirectly to the plant virus particle or VLP according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with the labeled, naturally occurring anti-ligands.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include compounds of the Alexa Fluor® series (Invitrogen™), fluorescein and its derivatives, rhodamine and its derivatives, dansyl, umbelliferone, and the like Chemiluminescent compounds include luciferin, and 2,3-dihydrophthalazinediones, e.g., luminol. For a review of various labeling or signal producing systems which may be used, see, U.S. Pat. No. 4,391,904, incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label.

Coatings on the Plant Virus Particle or VLP Exterior

In some embodiments, a coating can be added to the exterior of the plant virus particle to improve bioavailability. Administering an plant virus particle loaded with or conjugated to one or more of an imaging agent, an anticancer agent, and/or a targeting agent to a subject can sometimes generate an immune response. An "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, invading pathogens, cells or tissues infected with pathogens, or, in cases of autoimmunity or pathological inflammation, normal human cells or tissues. Components of an immune response can be detected in vitro by various methods that are well known to those of ordinary skill in the art. Generation of an immune response by the targeted viral particle is typically undesirable. Accordingly, in some embodiments it may be preferable to modify the plant virus particle or VLP-TRAIL conjugate or take other steps to decrease the immune response. For example, an immunosuppressant compound can be administered to decrease the immune response. More preferably, the plant virus particle or VLP can be modified to decrease its immunogenicity. Examples of methods suitable for decreasing immunity include attachment of anti-fouling (e.g., zwitterionic) polymers, glycosylation of the virus carrier, and PEGylation.

In some embodiments, the immunogenicity of the plant virus particle or VLP is decreased by PEGylation. PEGylation is the process of covalent attachment of polyethylene glycol (PEG) polymer chains to a molecule such as a targeted viral particle. PEGylation can be achieved by incubation of a reactive derivative of PEG with the targeted viral particle. The covalent attachment of PEG to the targeted viral particle can "mask" the agent from the host's immune system, and reduce production of antibodies against the carrier. PEGylation also may provide other benefits. PEGylation can be used to vary the circulation time of the targeted viral particle. For example, use of PEG 5,000 can provide a plant virus particle or VLP with a circulation half-life of about 12.5 minutes, while use of PEG 20,000 can provide a plant virus particle or VLP with a circulation half life of about 110 minutes.

The first step of PEGylation is providing suitable functionalization of the PEG polymer at one or both terminal positions of the polymer. The chemically active or activated derivatives of the PEG polymer are prepared to attach the PEG to the targeted viral particle. There are generally two methods that can be used to carry out PEGylation; a solution phase batch process and an on-column fed-batch process. The simple and commonly adopted batch process involves the mixing of reagents together in a suitable buffer solution, preferably at a temperature between 4 and 6° C., followed by the separation and purification of the desired product using a chromatographic technique.

An additional advantage to PEGylating the targeted virus particles is that PEGylation provides a convenient means for attaching additional compounds such as ligands for a tumor-associated receptor. For example, EGFR ligands can be conjugated to a plant virus particle or VLP via PEG spacers to enhance tissue-specificity and targeted delivery.

Cancer Treatment Using Plant Virus Particles or VLP-TRAIL Conjugate

Another aspect of the invention provides a method of treating cancer in a subject by administering a therapeutically effective amount of an agent including a plant virus particle or VLP conjugated to at least one TRAIL ligand. As used herein, agents including a plant virus particle or VLP-TRAIL conjugate can reach and preferably accumulate within cancer tissue after being administered to the subject. The ability of plant virus particles or VLPs themselves to target cancer tissue is supported by the biodistribution studies carried out by the inventors. See International Patent Publication WO/2013/181557. The disclosure of which is incorporated herein by reference. While not intending to be bound by theory, it appears that plant virus particles or VLPs, such as PVX, are taken up by blood components such as macrophage cells of the immune system, which subsequently accumulate in tumor tissue, thereby delivering the plant virus particle or VLP and the conjugated TRAIL ligand to the tumor cells.

In some embodiments, the virus particle can provide additional anticancer activity in addition to the apoptosis inducing effects of the TRAIL ligand. While not intending to be bound by theory, this additional anticancer therapy appears to be the result of an immunotherapeutic effect of the plant virus particles or VLPs themselves.

In some embodiments, the therapeutically effective amount in the amount the therapeutically effective amount is the amount required to activate caspase-dependent apoptosis via TRAIL-DR4/5 receptor binding in cancer cells of the subject. In some embodiments, the therapeutically effective amount is the amount required to decrease a tumor volume in a subject.

Agents including a plant virus particle or VLP conjugated to at least one TRAIL ligand described herein can be used to treat a variety of different types of cancer. "Cancer" or "malignancy" are used as synonymous terms and refer to any of a number of diseases that are characterized by uncontrolled, abnormal proliferation of cells, the ability of affected cells to spread locally or through the bloodstream and lymphatic system to other parts of the body (i.e., metastasize) as well as any of a number of characteristic structural and/or molecular features. A "cancer cell" refers to a cell undergoing early, intermediate or advanced stages of multi-step neoplastic progression. The features of early, intermediate and advanced stages of neoplastic progression have been described using microscopy. Cancer cells at each of the three stages of neoplastic progression generally have abnormal karyotypes, including translocations, inversion, deletions, isochromosomes, monosomies, and extra chromosomes. Cancer cells include "hyperplastic cells," that is, cells in the early stages of malignant progression, "dysplastic cells," that is, cells in the intermediate stages of neoplastic progression, and "neoplastic cells," that is, cells in the advanced stages of neoplastic progression.

The cancers treated by a method described herein can include the following: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, glioblastoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytoma and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, fallopian tube cancer, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In particular embodiments, the agent including a plant virus particle or VLP conjugated to at least one TRAIL ligand is used to treat a cancer selected from the group consisting of breast cancer, ovarian cancer, soft-tissue sarcoma, pancreatic cancer, colorectal cancer, non small cell lung cancer, lymphoma, non-Hodgkins lymphoma, and hepatocarcinoma.

In certain embodiments, the cancer treated is triple negative breast cancer. Triple negative breast cancer is a breast cancer where the three most common types of receptors known to fuel most breast cancer growth-estrogen, progesterone, and the HER-2/neu gene—are not present in the cancer tumor. This means that the breast cancer cells have tested negative for hormone epidermal growth factor receptor 2 (HER-2), estrogen receptors (ER), and progesterone receptors (PR). Since the tumor cells lack the necessary receptors, common treatments like hormone therapy and drugs that target estrogen, progesterone, and HER-2 are ineffective.

Additional Cancer Therapeutics

In some embodiments, in addition to administering an agent including a plant virus particle or VLP conjugated to at least one TRAIL ligand, the method of treating cancer in a subject can further include the step of administering a therapeutically effective amount of a cancer therapeutic or cancer therapy to the subject. A "cancer therapeutic" or "cancer therapy", as used herein, can include any agent or treatment regimen that is capable of negatively affecting cancer in an animal, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of an animal with cancer. Cancer therapeutics can include one or more therapies such as, but not limited to, chemotherapies, radiation therapies, hormonal therapies, and/or biological therapies/immunotherapies. A reduction, for example, in cancer volume, growth, migration, and/or dispersal in a subject may be indicative of the efficacy of a given therapy.

In some embodiments, the method can further include the step of administering a therapeutically effective amount of an anticancer therapeutic agent to the subject. The anticancer therapeutic agents can be in the form of biologically active ligands, small molecules, peptides, polypeptides, proteins, DNA fragments, DNA plasmids, interfering RNA molecules, such as siRNAs, oligonucleotides, and DNA encoding for shRNA. In some embodiments, cytotoxic compounds are included in an anticancer agent described herein. Cytotoxic compounds include small-molecule drugs such as doxorubicin, mitoxantrone, methotrexate, and pyrimidine and purine analogs, referred to herein as antitumor agents.

The anticancer therapeutic agent can include an anticancer or an antiproliferative agent that exerts an antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms such as biological response modification. There are large numbers of anti-proliferative agent agents available in commercial use, in clinical evaluation and in pre-clinical development. For convenience of discussion, anti-proliferative agents are classified into the following classes, subtypes and species: ACE inhibitors, alkylating agents, angiogenesis inhibitors, angiostatin, anthracyclines/DNA intercalators, anti-cancer antibiotics or antibiotic-type agents, antimetabolites, antimetastatic compounds, asparaginases, bisphosphonates, cGMP phosphodiesterase inhibitors, calcium carbonate, cyclooxygenase-2 inhibitors, DHA derivatives, DNA topoisomerase, endostatin, epipodophylotoxins, genistein, hormonal anticancer agents, hydrophilic bile acids (URSO), immunomodulators or immunological agents, integrin antagonists, interferon antagonists or agents, MMP inhibitors, miscellaneous antineoplastic agents, monoclonal antibodies, nitrosoureas, NSAIDs, ornithine decarboxylase inhibitors, pBATTs, radio/chemo sensitizers/protectors, retinoids, selective inhibitors of proliferation and migration of endothelial cells, selenium, stromelysin inhibitors, taxanes, vaccines, and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category.

Examples of anticancer therapeutic agents that can be administered in combination with a plant virus or virus-like particle described herein include Taxol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; temozolomide, teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other anticancer therapeutic agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cyclopatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; silicon phthalocyanine (PC4) sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosamOinoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thalidomide; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B;

vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Other anticancer agents can include the following marketed drugs and drugs in development: Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Arnad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-IAABE (Cytoskeleton/Mt. Sinai School of Medicine), A-204197 (Abbott), T-607 (Tularik, also known as T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

Still other anticancer therapeutic agents include alkylating agents, such as nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.), antimetabolites, such as folic acid analog (e.g., methotrexate), or pyrimidine analogs (e.g., fluorouracil, floxouridine, Cytarabine), purine analogs (e.g., mercaptopurine, thioguanine, pentostatin, vinca alkaloids (e.g., vinblastin, vincristine), epipodophyllotoxins (e.g., etoposide, teniposide), platinum coordination complexes (e.g., cisplatin, carboblatin), anthracenedione (e.g., mitoxantrone), substituted urea (e.g., hydroxyurea), methyl hydrazine derivative (e.g., procarbazine), adrenocortical suppressant (e.g., mitotane, amino glutethimide).

In particular embodiments, anticancer agents include angiogenesis inhibitors such as angiostatin K1-3, DL-α-difluoromethyl-ornithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, melphalan, mitoxantrone, and oxaliplatin; DNA synthesis inhibitors such as methotrexate, 3-Amino-1,2,4-benzotriazine 1,4-dioxide, aminopterin, cytosine β-D-arabinofuranoside, 5-Fluoro-5'-deoxyuridine, 5-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-β-D-ribofuranoside, etoposine, formestane, fostriecin, hispidin, cyclocreatine, mevinolin, trichostatin A, tyrophostin AG 34, and tyrophostin AG 879, Gene Regulating agents such as 5-aza-2'-deoxycitidine, 5-azacytidine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin, rapamycin, thapsigargin, and bikunin, and derivatives (as defined for imaging agents) thereof.

In some embodiments, the method can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, immunotherapy, and administration of immunotoxins.

In some embodiments, the step of ablating the cancer includes immunotherapy of the cancer. Cancer immunotherapy is based on therapeutic interventions that aim to utilize the immune system to combat malignant diseases. It can be divided into unspecific approaches and specific approaches. Unspecific cancer immunotherapy aims at activating parts of the immune system generally, such as treatment with specific cytokines known to be effective in cancer immunotherapy (e.g., IL-2, interferon's, cytokine inducers).

In contrast, specific cancer immunotherapy is based on certain antigens that are preferentially or solely expressed on cancer cells or predominantly expressed by other cells in the context of malignant disease (usually in vicinity of the tumor site). Specific cancer immunotherapy can be grouped into passive and active approaches.

In passive specific cancer immunotherapy substances with specificity for certain structures related to cancer that are derived from components of the immune system are administered to the patient. The most prominent and successful approaches are treatments with humanized or mouse/human chimeric monoclonal antibodies against defined cancer associated structures (such as Trastuzumab, Rituximab, Cetuximab, Bevacizumab, Alemtuzumab). The pharmacologically active substance exerts is activity as long as a sufficient concentration is present in the body of the patient, therefore administrations have to be repeated based on pharmacokinetic and pharmacodynamic considerations.

On the other hand, active specific cancer immunotherapy aims at antigen-specific stimulation of the patient's immune system to recognize and destroy cancer cells. Active specific cancer immunotherapy therefore, in general, is a therapeutic vaccination approach. There are many types of cancer vaccine approaches being pursued, such as vaccination with autologous or allogeneic whole tumor cells (in most cases genetically modified for better immune recognition), tumor cell lysates, whole tumor associated antigens (produced by means of genetic engineering or by chemical synthesis), peptides derived from protein antigens, DNA vaccines encoding for tumor associated antigens, surrogates of tumor antigens such as anti-idiotypic antibodies used as vaccine antigens, and the like. These manifold approaches are usually administered together with appropriate vaccine adjuvants and other immunomodulators in order to elicit a quantitatively and qualitatively sufficient immune response (many novel vaccine adjuvant approaches are being pursued in parallel with the development of cancer vaccines). Another set of cancer vaccine approaches relies on manipulating dendritic cells (DC) as the most important antigen presenting cell of the immune system. For example, loading with tumor antigens or tumor cell lysates, transfection with genes encoding for tumor antigens and in-vivo targeting are suitable immunotherapies that can be used together with the virus or virus-like particles of the invention for cancer treatment.

In some embodiments where the plant virus particle is loaded with or conjugated to an imaging agent, the method can further include the step of imaging the cancer tissue in the subject using an imaging device. Examples of imaging methods include computed tomography, positive emission tomography, and magnetic resonance imaging. "Computed tomography (CT)" refers to a diagnostic imaging tool that computes multiple x-ray cross sections to produce a cross-sectional view of the vascular system, organs, bones, and tissues. "Positive emissions tomography (PET)" refers to a diagnostic imaging tool in which the patient receives a radioactive isotopes by injection or ingestion which then computes multiple x-ray cross sections to produce a cross-sectional view of the vascular system, organs, bones, and tissues to image the radioactive tracer. These radioactive isotopes are bound to compounds or drugs that are injected into the body and enable study of the physiology of normal and abnormal tissues. "Magnetic resonance imaging (MRI)" refers to a diagnostic imaging tool using magnetic fields and radiowaves to produce a cross-sectional view of the body including the vascular system, organs, bones, and tissues.

Administration and Formulation of Targeted Viral Particles

The methods of the invention include administering to a subject, preferably a mammal, and more preferably a human, the agent of the invention in an amount effective to produce the desired effect. In some embodiments, the agent including a plant virus or VLP conjugated to TRAIL is administered together with a pharmaceutically acceptable carrier to provide a pharmaceutical formulation. The plant virus or VLP may be present in a pharmaceutical composition in an amount from 0.001 to 99.9 wt %, more preferably from about 0.01 to 99 wt %, and even more preferably from 0.1 to 95 wt %.

Pharmaceutically acceptable carriers enable the agent to be delivered to the subject in an effective manner while minimizing side effects, and can include a variety of diluents or excipients known to those of ordinary skill in the art. Formulations include, but are not limited to, those suitable for oral, rectal, vaginal, topical, nasal, ophthalmic, or parental (including subcutaneous, intramuscular, intraperitoneal, intratumoral, and intravenous) administration. For example, for parenteral administration, isotonic saline is preferred. For topical administration, a cream, including a carrier such as dimethylsulfoxide (DMSO), or other agents typically found in topical creams that do not block or inhibit activity of the compound, can be used. Other suitable carriers include, but are not limited to, alcohol, phosphate buffered saline, and other balanced salt solutions.

A pharmaceutically acceptable carrier for a pharmaceutical composition can also include delivery systems known to the art for entraining or encapsulating drugs, such as anti-cancer drugs. In some embodiments, the disclosed compounds can be employed with such delivery systems including, for example, liposomes, nanoparticles, nanospheres, nanodiscs, dendrimers, and the like. See, for example Farokhzad, O. C., Jon, S., Khademhosseini, A., Tran, T. N., Lavan, D. A., and Langer, R. (2004). "Nanoparticle-aptamer bioconjugates: a new approach for targeting prostate cancer cells." Cancer Res., 64, 7668-72; Dass, C. R. (2002). "Vehicles for oligonucleotide delivery to tumours." J. Pharm. Pharmacol., 54, 3-27; Lysik, M. A., and Wu-Pong, S. (2003). "Innovations in oligonucleotide drug delivery." J. Pharm. Sci., 92, 1559-73; Shoji, Y., and Nakashima, H. (2004). "Current status of delivery systems to improve target efficacy of oligonucleotides." Curr. Pharm. Des., 10, 785-96; Allen, T. M., and Cullis, P. R. (2004). "Drug delivery systems: entering the mainstream." Science, 303, 1818-22. The entire teachings of each reference cited in this paragraph are incorporated herein by reference.

The formulations may be conveniently presented in unit dosage form and may be prepared by any of the methods well known in the art of pharmacy. Preferably, such methods include the step of bringing the targeted viral particles into association with a pharmaceutically acceptable carrier that constitutes one or more accessory ingredients. In general, the formulations are prepared by uniformly and intimately bringing the targeted viral particles into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The formulated targeted viral particles can be administered as a single dose or in multiple doses.

Useful dosages of the agents can be determined by comparing their in vitro activity and the in vivo activity in animal models. Methods for extrapolation of effective dosages in mice, and other animals, to humans are known in the art; for example, see U.S. Pat. No. 4,938,949. An amount adequate to accomplish therapeutic or prophylactic treatment is defined as a therapeutically- or prophylactically-effective dose.

Single or multiple administrations of the compositions may be administered depending on the dosage and frequency as required and tolerated by the subject. In both prophylactic and therapeutic regimes, agents are usually administered in several dosages until an effect has been achieved. A pharmaceutically acceptable composition containing the plant virus, virus-like particle, and/or additional cancer therapeutic can be administered at regular intervals, depending on the nature and extent of the cancer's effects, and on an ongoing basis. Administration at a "regular interval," as used herein, indicates that the therapeutically effective amount is administered periodically (as distinguished from a one-time dose). In one embodiment, the pharmaceutically acceptable composition including the plant virus particle or VLP-TRAIL conjugate, and/or an additional cancer therapeutic is administered periodically, e.g., at a regular interval (e.g., bimonthly, monthly, biweekly, weekly, twice weekly, daily, twice a day or three times or more often a day).

The administration interval for a single individual can be fixed, or can be varied over time, depending on the needs of the individual. For example, in times of physical illness or stress, or if disease symptoms worsen, the interval between doses can be decreased.

For example, the administration of a plant virus or virus like particle and/or the additional therapeutic agent can take place at least once on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least once on week 1, 2, 3, 4, 5, 6, 7, 8, 9, 10, 11, 12, 13, 14, 15, 16, 17, 18, 19 or 20, or any combination thereof, using single or divided doses of every 60, 48, 36, 24, 12, 8, 6, 4, or 2 hours, or any combination thereof. Administration can take place at any time of day, for example, in the morning, the afternoon or evening. For instance, the administration can take place in the morning, e.g., between 6:00 a.m. and 12:00 noon; in the afternoon, e.g., after noon and before 6:00 p.m.; or in the evening, e.g., between 6:01 p.m. and midnight.

Effective doses of the filamentous plant virus carrier vary depending upon many different factors, including means of administration, target site, physiological state of the patient, whether the patient is human or an animal, other medications administered, and whether treatment is prophylactic or therapeutic. In any event, the administration regime should provide a sufficient quantity of the composition of this invention to effectively treat the subject.

The dosage for administering an agent described herein for the treatment of cancer ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. A suitable amount of plant virus particle or VLP is used to provide the desired dosage. The agent is usually administered on multiple occasions. Alternatively, the agent can be administered as a sustained release formulation, in which case less frequent administration is required. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes). In some embodiments, the frequency of administration of a plant virus or VLP-TRAIL conjugate agent can pose challenging for clinical implementation. Therefore, in some embodiments, the agent is administered in situ to a subject and can be formulated in a slow release formulation in order to sustain immune stimulation by maintaining a therapeutic concentration of the plant virus or virus-like nanoparticle in situ while alleviating the need for frequent administrations. In some embodiments, a slow release formulation can include a polymer-based hydrogel or a dendrimer.

For parenteral administration, the agents can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

The present invention is illustrated by the following examples. It is to be understood that the particular examples, materials, amounts, and procedures are to be interpreted broadly in accordance with the scope and spirit of the invention as set forth herein.

EXAMPLES

Example 1

Presentation and Delivery of TRAIL Via Elongated Viral Nanoparticle Enhances Antitumor Efficacy In this Example, we describe the development of the flexuous, filamentous potato virus X nanoplatform for the delivery of TRAIL. Potato virus X (PVX) is a plant virus belonging to the Potexvirus group. The virion is assembled from 1270 identical 25-kDa coat proteins (CPs) units orderly arranged around its single-stranded RNA; the assembled construct results in a flexuous elongated nanoparticles (NP) measuring 515 nm in length and 13 nm in diameter. Via mechanical inoculation and extraction from *Nicotiana benthamiana* leaves, ~20 mg of PVX is typically obtained from 100 g of infected leaf material. Being a biologic nanotechnology, PVX particles are obtained with a high degree of reproducibility and monodispersity. These qualities are important factors for quality control and assurance (QC/QA). The viral NP, with multiple surface exposed residues, such as lysine and cysteine, can be readily modified to load not only single but multiple modules such as peptide ligands or epitopes as well as fluorescent probes and MRI contrast agents. Hydrophobic drugs, such as, doxorubicin can also be loaded into grooves of the protein assembly via hydrophobic interactions. In agreement with observations in synthetic anisotropic systems, PVX was demonstrated to have enhanced tumor homing compared to its spherical viral counterpart, cowpea mosaic virus.

To develop therapeutic TRAIL-loaded PVX, we utilized non-covalent conjugation based on the coordination bonds between Nickel coordinated nitrilotriacetic acid (Ni-NTA) modules displayed on PVX surface and TRAIL with an N-terminal His-tag (FIG. 4). This method offers several advantages vs. traditional bioconjugation strategies: (1) PVX with multiple surface-exposed lysines can be targeted to display up to more than 1000-1500 small chemical modifiers (Ni-NTA) per particle; the conjugation of high molecular weight molecules such as proteins or enzymes to viral nanoparticle systems generally yields lower conjugation efficiencies. (2) As most recombinant proteins expressed from bacterial systems typically incorporate a His-tag for purification either at the N- or C-terminus, no modification post-harvest and purification is required for TRAIL conjugation, thus reducing the heterogeneity in chemical conjugation without disruption of native structures. (3) The conjugation step is simple, by mixing the Ni-NTA displayed nanostructure (here PVX) and His-tagged protein of interest (here TRAIL) in buffer solutions, pH 7.4. (4) With the specific binding of TRAIL to PVX via its designated N-terminal His-tag, orientational control is provided, allowing for the bioactive TRAIL at the C-terminus to be solvent-exposed upon nanoparticle display, therefore mimicking its membrane-bound state when in contact with surface-overexpressed DR4/5 receptors on cancer cells.

We have developed the following protocol to construct the viral NP-therapeutic protein complex: PVX was first conjugated at its solvent-exposed lysine residues to display nitrilotriacetic acid (PVXNTA) using a click chemistry protocol for the particle. Subsequently, PVX-NTA suspension was dialyzed towards PBS buffer, pH 7.4, containing 1 mM Ni2+ for Ni-NTA chelate formation on PVX. Excess Ni2+ ions were removed by additional dialysis in PBS buffer. The resulting particle is referred as PVX-Ni. Described further below (FIG. 5). The presence of Ni-NTA conjugated on the viral NP was qualitatively confirmed by addition of 1,4-Dithiothreitol (DTT) 100 mM final concentration; the reducing reagent converted the solution from transparent into yellow, brownish color, indicating the reduction of Ni2+ ions.

Figure 6A:
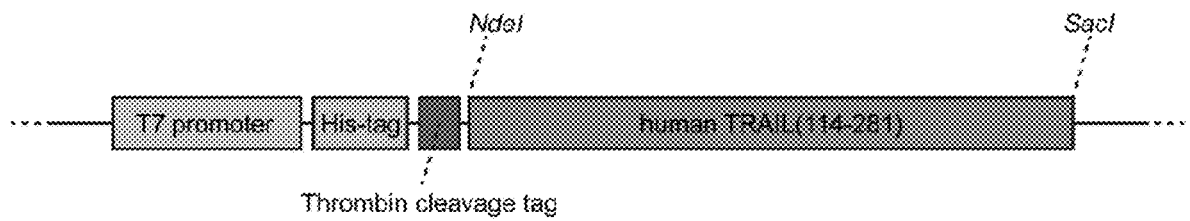

The therapeutic protein, HisTRAIL, with an N-terminal His-tag, was expressed in ClearColi BL21(DE)3 carrying pET-28a(+)/HisTRAIL plasmid encoding the amino acid (aa) 114-281 sequence of human TRAIL, the region responsible for TRAIL bioactivity. HisTRAIL has a designated N-terminal His-tag, followed by a thrombin cleavage sequence allowing for removal of the His-tag if desired (FIG. 6A). HisTRAIL was purified using metal affinity chromatography under native condition. Details of expression, purification, and characterization of HisTRAIL by gel electrophoresis and western blot analysis are described in FIG. 6B. It should be noted that in recombinant TRAIL expression, dimers formed via intermolecular disulfide bridge between Cys230 typically coexist with TRAIL monomers, while unpaired Cys 230 is essential for bioactive TRAIL trimer formation and TRAIL/receptor interactions. Therefore, purified HisTRAIL was treated by 10 mM DTT for 1 h at room temperature, and followed by dialysis in PBS buffer, pH 7.4, to remove excess DTT and allow TRAIL trimer formation.

To construct the PVX-HisTRAIL complex, the reaction conditions were optimized in terms of buffer conditions, ratio of reagents, and reaction time; the optimal loading protocol was defined as: mixing PVX particle and purified HisTRAIL at a 1:900 molar ratio for 2 h at room temperature in PBS, pH 7.4. The reaction mix was purified by ultracentrifugation (212,000×g, 3 h, 4° C.) to remove unbound HisTRAIL. The pellet was resuspended in PBS, pH 7.4 overnight to obtain the PVX-HisTRAIL suspension.

Figure 1A:
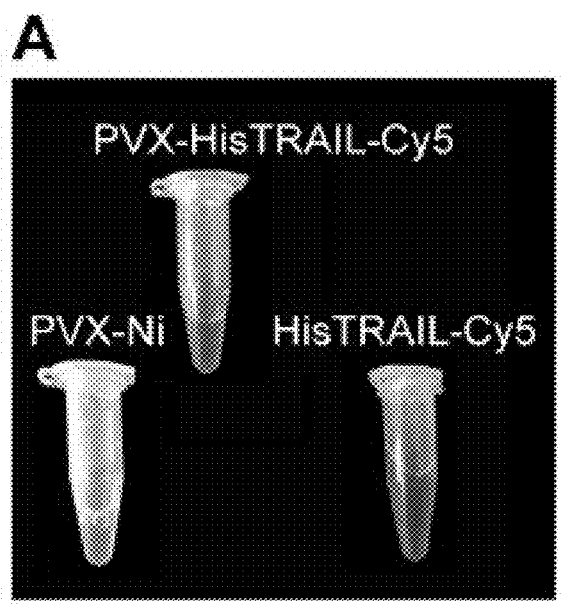
FIGS. 1(A-E) illustrate the characterization of PVX-HisTRAIL-Cy5. (A) As-prepared PVX-Ni suspension (transparent), PVX-HisTRAIL-Cy5 suspension (blue), and TRAIL-Cy5 solution (blue). (B) Size exclusion chromatography (SEC) profiles of the corresponding PVX-based nanoparticle preparations. The inset shows co-elution of His-TRAILCy5 (absorbance 647 nm) with PVX (absorbance 260 nm, 280 nm). (C) Agarose gel electrophoresis of (1) PVX-Ni, (2) PVX-HisTRAIL-Cy5, and (3) HisTRAIL-Cy5. The samples were visualized upon fluorescent excitation at 632 nm (red) and after Coomassie blue (CB) staining under white light. (D) TEM images of negative stained PVXHis-TRAIL-biotin vs. PVX-Ni, stained with anti-biotin antibodies conjugated with gold nanoparticles. (E) Quantitative analysis of PVX-HisTRAIL by SDS-PAGE and western blot. In SDS-PAGE, (1) PVX-Ni, (2) HisTRAIL, and (3) PVX-HisTRAIL in the presence of DTT, were run in 4-12% NuPAGE gel in 1×MOPS running buffer. Separated PVX CP and HisTRAIL were indicated by the red and green arrows, respectively. To determine PVX and HisTRAIL amounts by western blot (stained with either anti-TRAIL or anti-PVX antibodies), the PVX-HisTRAIL conjugate was loaded at either original concentration (4) or 10× dilution (4*) so that protein amounts lie within linear range of standard curves.
Figure 1B:
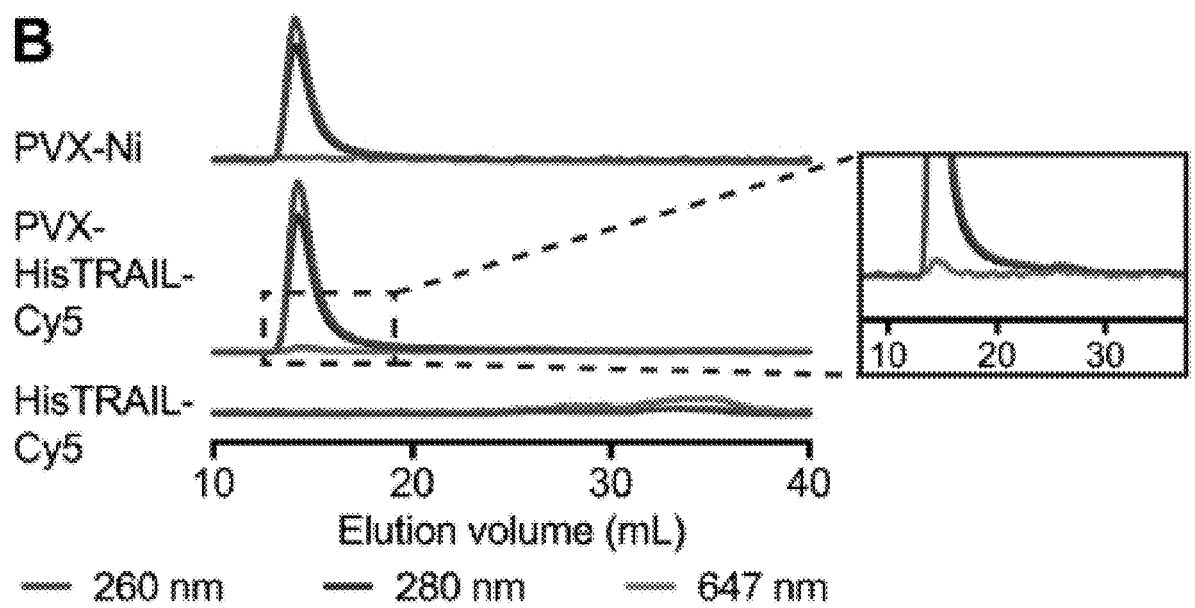

To visualize the presentation of HisTRAIL on PVX, we utilized a Cy5-labeled HisTRAIL, referred as HisTRAIL-Cy5 (FIG. 7), for preparing PVX-HisTRAIL-Cy5 conjugate as described above. After purification, the obtained conjugate suspension exhibits a blue color derived from the present of Cy5 (FIG. 1A). Size exclusion chromatography (SEC) was conducted to confirm the intact filamentous structure in PVX-Ni as well as PVX-HisTRAILCy5 after complexation and purification (FIG. 1B). Both of the PVX-based nanostructures eluted from the Superose6 column at 14.5 mL, similar to one in native PVX (FIG. 8). In addition, PVX-HisTRAIL-Cy5 absorbed light at 647 nm at the elution peak of the particle (FIG. 1B), indicating the attachment of HisTRAIL-Cy5. Free HisTRAIL-Cy5 elutes at X-Y mL; for the PVXHisTRAIL-Cy5 samples, no peaks were detectable at this elution volume, indicating a purified PVX-HisTRAIL preparation without presence of free HisTRAIL. The absorbance ratios of 260/280 nm were determined as 1.19 and 1.22 for PVX-HisTRAIL-Cy5 and PVX-Ni, respectively. The shift toward the 280 nm absorbance (the 280 nm peak is indicative of protein, while 260 nm is a measure for RNA content) for the PVX-HisTRAIL-Cy5 formulation is another indicator of HisTRAILCy5 loading.

Figure 1C:
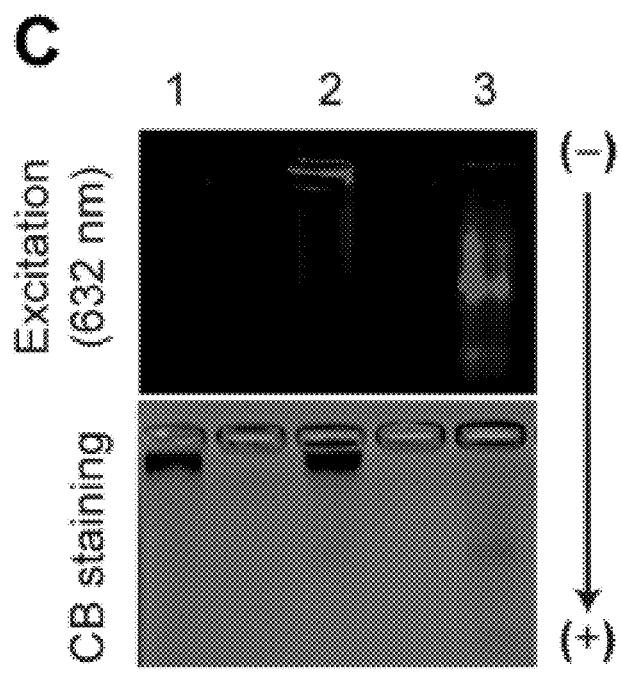

Native gel electrophoresis (0.8% agarose gel, run at 100 V, for 40 min in TBE buffer, FIG. 1C) was in agreement with SEC, also indicating successful complexation of HisTRAIL-Cy5 with PVX: free HisTRAIL-Cy5 shows mobility toward the anode while PVX particle being a large macromolecule does show a small degree of migration toward the anode, but the majority of the samples remain in the pockets of the gel. Co-localization of the fluorescent HisTRAIL-Cy5, detected either by excitation at 632 nm (red) light source or after CB staining and visualization under white light, with PVX, detected after CB staining under white light, is indicative of successful TRAIL-to-PVX loading. Again, free HisTRAIL-Cy5 was not apparent in this method.

Figure 1D:
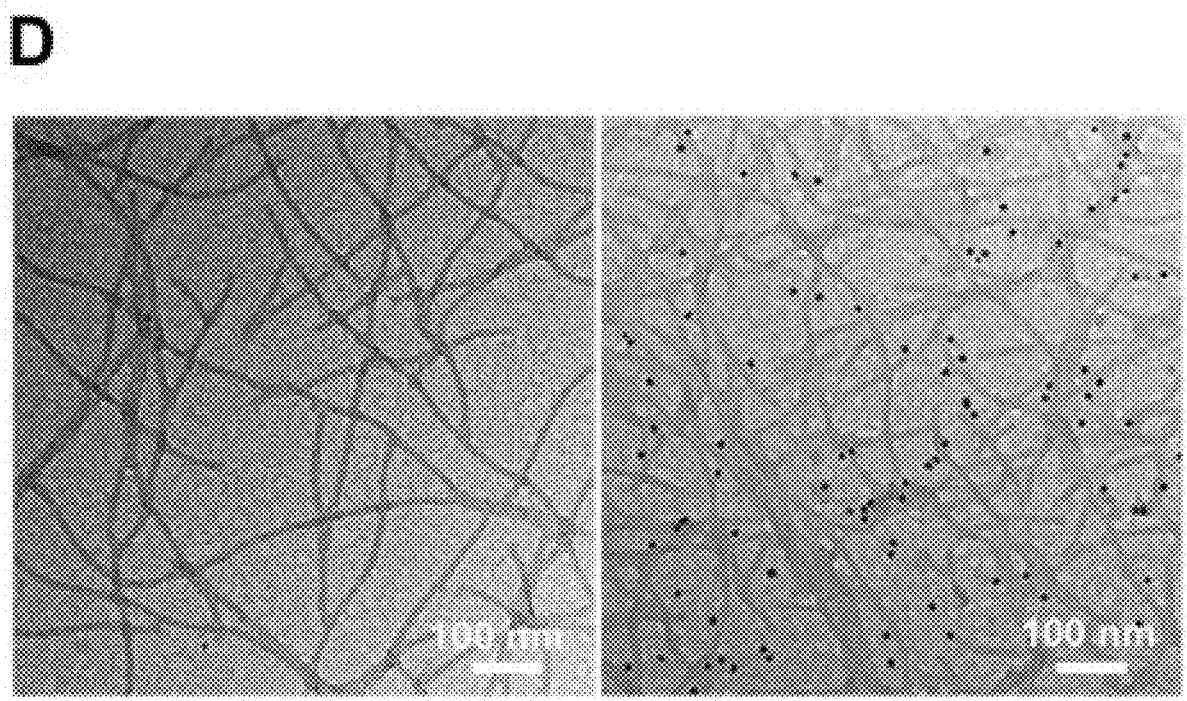

Lastly, to confirm the structural integrity of TRAIL-displaying PVX filaments, we made use of an immunogold-labeling protocol: similar to PVX-HisTRAIL-Cy5 preparation, HisTRAIL was first biotinylated using biotin N-hydroxysuccinimide ester to provide a tag for immune staining (FIG. 9). PVXHisTRAIL-biotin prepared by the described method was loaded onto the TEM grid at 0.1 mg mL-1, and was fixed by 2.5% (v/v) glutaraldehyde in 10 min. After washing by PBS buffer, the sample was blocked, and then stained with anti-biotin antibodies conjugated on a 10-nm gold nanoparticles diluted 5 times in PBS buffer. After several washes, samples were negative-stained using 2% (w/v) uranyl acetate. PVX-Ni sample was also prepared as a control. The typical filamentous structures for imaged by TEM confirming structural integrity for both, PVX-Ni and PVX-HisTRAIL-biotin samples (FIG. 1D). PVX-bound gold nanoparticles were observed in the case of PVX- HisTRAIL-biotin, demonstrating the multivalent display of TRAIL on the PVX nanoplatform technology (FIG. 1D).

Figure 1E:
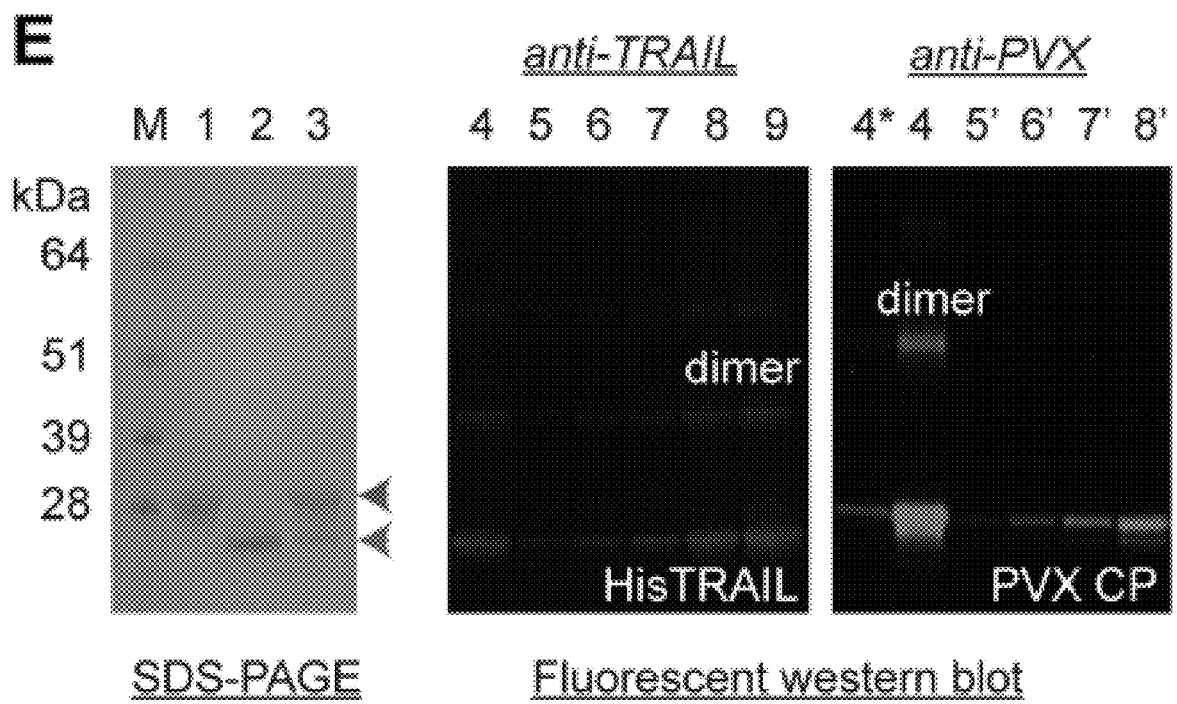

The combination of methods utilizing Cy5- and biotin-tagged TRAIL described above provide confidence in the TRAIL conjugation and display method. Next, we developed the therapeutic PVX-HisTRAIL conjugate. Validation of complexation of the non-chemically modified HisTRAIL to PVX was confirmed and quantified by SDSPAGE and western blot (FIG. 1E). 5 μg of PVX-Ni, His-TRAIL, and PVX-HisTRAIL were separated on a 4-12% NuPAGE gel. DTT was added to the sample mixtures to reduce nickel and possible disulfide bonds and to separate bound HisTRAIL from PVX CP. As a result, the corresponding individual bands of the PVX CP (25 kDa) and HisTRAIL (22 kDa) were observed after CB staining. Analysis of SDS-PAGE data using band analysis tool and ImageJ software indicated a 32% weight ratio of HisTRAIL to PVX CP. These data were further validated by western blot using rabbit anti-PVX and rabbit anti-TRAIL primary antibodies, respectively, followed by staining with anti-rabbit secondary antibodies conjugated with IRDye 800 CW (774/789 nm). Quantitative data were obtained by imaging under infrared light using FluorChem R instrument. The detailed experimental procedures are described below. Data were in good agreement with SDS-PAGE and indicated 2.45 μg HisTRAIL per 7.93 μg PVX CP, i.e. a protein weight ratio of 30.8%.

Using the known molecular weights of HisTRAIL (22 kDa) and PVX particle (36×105 kDa), ~489 HisTRAIL molecules were attached on PVX particle, which equals to ~1/3 PVX CPs were conjugated with a HisTRAIL molecule. Considering 900 molecules per particle were added, the yield of the conjugation is >50%, attesting to the effectiveness of the non-covalent display strategy.

Figure 2A:
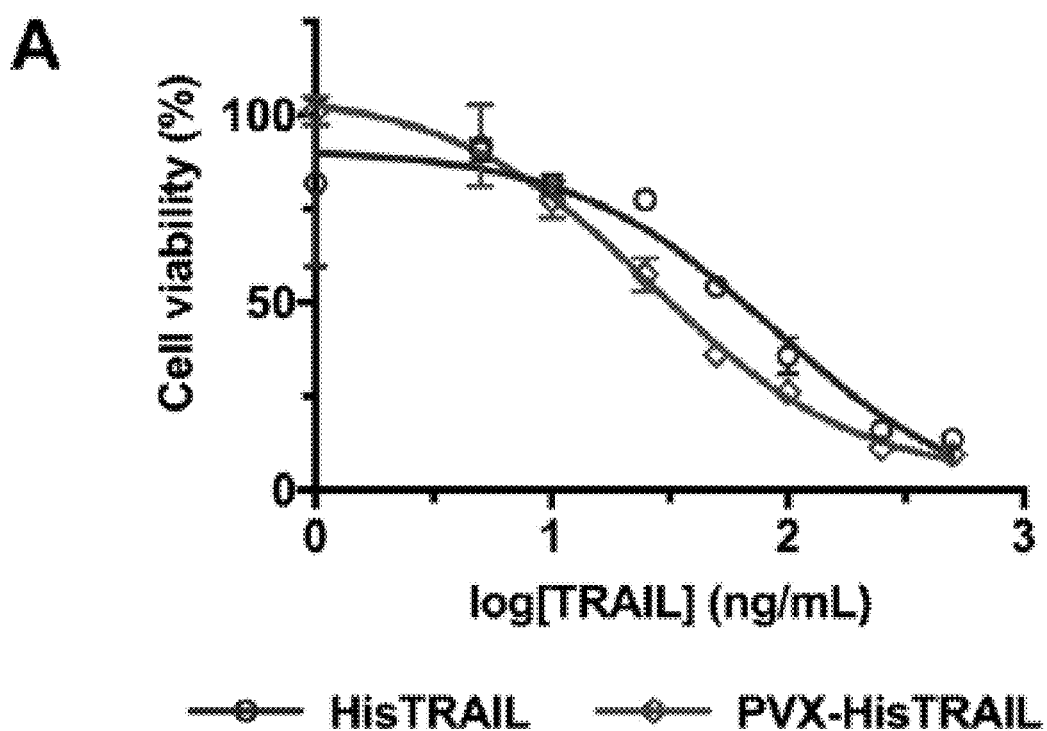

We then set out to evaluate the anticancer efficacy of the PVX-HisTRAIL therapeutic nanoparticle in parallel with HisTRAIL determined by MTT cytotoxicity assay. Herein, a panel of triple negative breast cancer (TNBC) cell lines, MDA-MB-231, HCC-38, and BT-549, were used. Increasing concentrations of the TRAIL protein or the PVXHis-TRAIL conjugate were incubated with cells for 12 h to trigger apoptosis. A representative data set of the concentration-dependent effect of TRAIL vs. PVX-HisTRAIL on MDA-MB-231 cell viability is shown in FIG. 2A. Both HisTRAIL and PVX-HisTRAIL exhibit cytotoxic bioactivity with PVX-HisTRAIL outperforming free TRAIL. The IC50 value for PVX-HisTRAIL was determined at 26.7 ng/mL, which is a 3.25-fold lower than the IC50 for His-TRAIL (86.6 ng/mL). PVX-Ni did not exhibit cell toxicity at the highest corresponding concentration in PVX-His-TRAIL, confirming the biocompatibility of the delivery platform. An even more profound effect was observed in other TNBC cell lines (Table 1), with 9.9-fold and 9.3-fold lower in IC50 values for PVX-HisTRAIL vs. free His-TRAIL using HCC-38 and BT-549 cell lines, respectively. Neither PVX-HisTRAIL nor HisTRAIL did induce apoptosis in SK-BR-3, the HER-2 amplified breast cancer cell line (FIG. 10). These data are consistent with previous reports that indicate effectiveness of TRAIL therapy in TNBC but not HER-2 positive breast cancer. Given that TNBC is an aggressive, life-threatening breast cancer subtypes, whose available treatment is limited to chemotherapy, this "PVX-bound" TRAIL concept might be a promising approach for TRAIL-based therapy for future TNBC treatment.

TABLE 1

$IC_{50}$ values (ng/mL) of HisTRAIL vs. PVC-HisTRAIL in various TNBC models, determined by GraphPad Prism software

|  | MDA-MB-231 | HCC-38 | BT-549 |
| --- | --- | --- | --- |
| HiTRAIL | 86.8 | 367.2 | 543.0 |
| PVX-HisTRAIL | 26.7 | 36.8 | 58.0 |

Figure 2B:
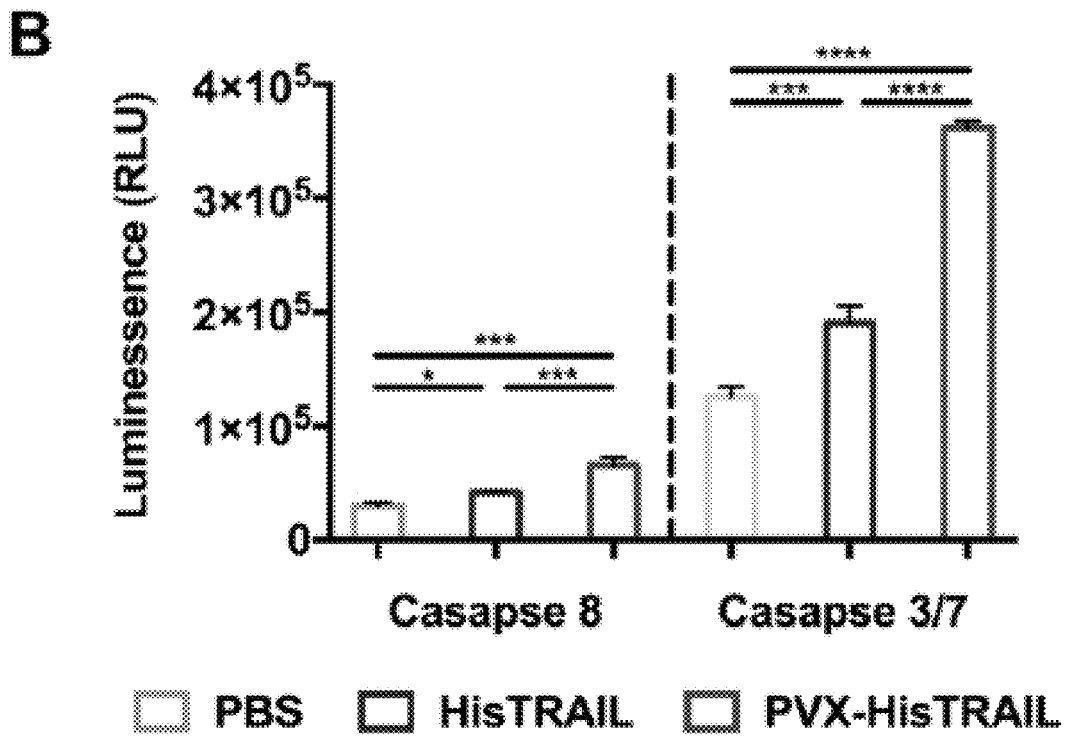

TRAIL-DR4/5 receptor binding activates caspase-dependent apoptosis. Specifically, TRAIL-DR4/5 receptor binding induces receptor oligomerization, followed by the recruitment of FAS-associated protein with death domain (FADD) and pro-caspase-8 to form a functional death-inducing signaling complex (DISC) at the plasma membrane. Subsequently, caspase-8 is activated and released into the cytosol, where it cleaves and activates caspase-3 or -7 to execute the apoptosis in cancer cells (FIG. 4). Therefore, we determined differences in levels of caspase-8 and caspase-3/7 activated by HisTRAIL or PVX-HisTRAIL in MDA-MB-231 model (FIG. 2B). The drugs were incubated with MDA-MB-231 cells for 3 h before adding reagents from Caspase-Glo 8 and Caspase-Glo 3/7 Assay Kit. The assay was performed as per manufacturer's instructions. At a dose of 20 ng mL-1 HisTRAIL, the level of caspase 8 in PVX-HisTRAIL increased about 2-fold compared to the PBS control, while free His-TRAIL protein only increased caspase 8 levels by 1.38 fold compared to PBS. The resulting caspase 3/7 showed a similar trend with a 2.9-fold increase for PVX-HisTRAIL and a 1.5-fold for His-TRAIL vs. PBS controls. These data are consistent with results from cell viability assays and data indicate that surface-bound TRAIL delivered and displayed by PVX is more effective in that it activates caspases leading to apoptosis of TNBC cells.

Figure 3A:
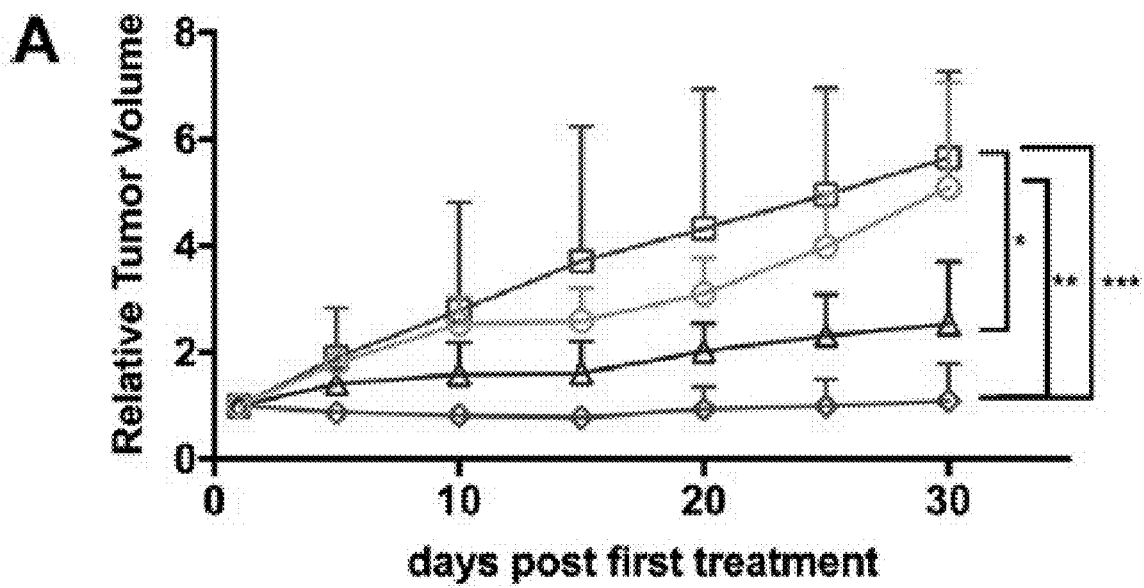
Figure 3B:
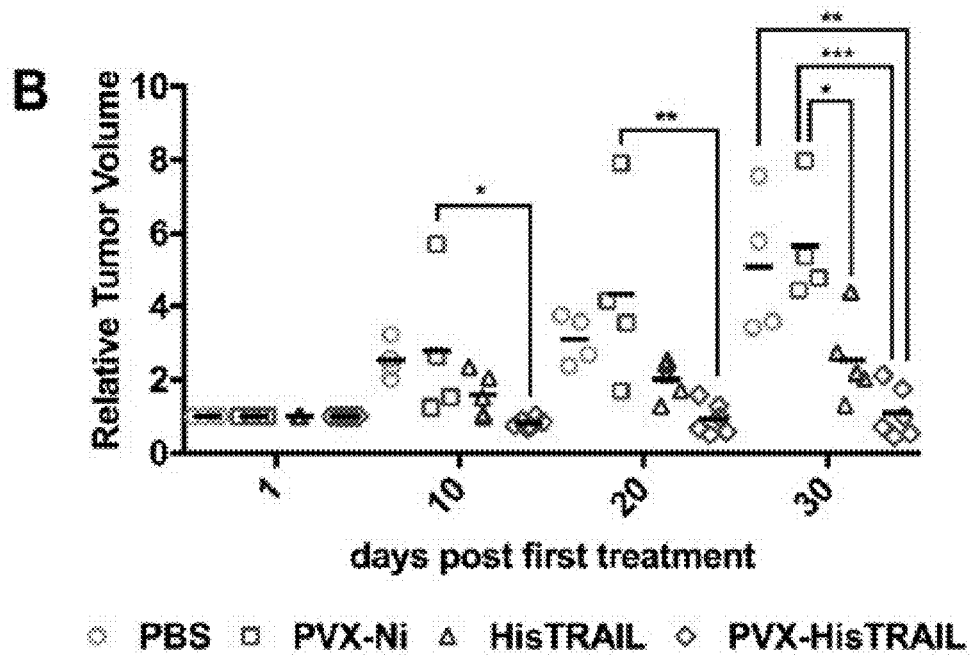
Figure 3C:
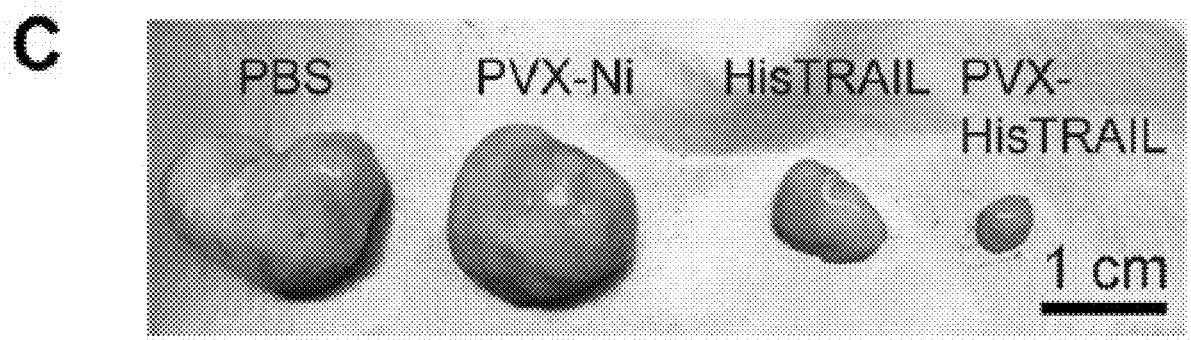

Based on the promising performance of PVX-HisTRAIL in vitro, we continued investigating the tumor-inhibiting effects in an athymic nude mouse model bearing subcutaneous MDA-MB-231 tumors. Treatment started when the tumor volume reached 100-150 $mm^3$. PVX-HisTRAIL or HisTRAIL was injected intratumorally every 2 days at the dose of 5 μg His-TRAIL/injection. PBS and PVX-Ni, at the corresponding particle amount injected for PVX-HisTRAIL (~12-15 μg particle per injection), were used as controls. While we envision systemic administration for clinical applications, we started here by evaluating intratumoral treatments to focus on the question as to whether PVX-delivered HisTRAIL would outperform free HisTRAIL; the intratumoral treatment allows one to precisely control and match the dosing, and, thus, eliminates confounding factors from varying biodistribution. We chose a dose of 5 μg His-TRAIL per tumor. Mice were randomly assigned with HisTRAIL: n=5, PVX-HisTRAIL: n=6, PVX-Ni: n=4, and PBS: n=4; tumor volumes were monitored daily, and the total volumes were normalized to initial tumor volume at the treatment starting day. Changes in tumor volume during treatment and distribution of individual tumor volume in each group are shown in FIGS. 3A and B, respectively. Both HisTRAIL and PVX-HisTRAIL demonstrate efficacy with PVX-HisTRAIL outperforming free TRAIL. The PVX-Ni carrier has no efficacy compared to the PBS control group. At day 30 post first treatment, average relative tumor volume increased by 5.65-fold and 5.09-fold for PVX-Ni and PBS group, respectively. In stark contrast tumor volumes for the free HisTRAIL treatment group only increased by 2.53-fold, while there was essentially no increase in tumor volume for the group treated with PVX-HisTRAIL (increase was 1.09 fold vs. starting volume; FIG. 3A). Statistically significant difference between PVX-HisTRAIL and the controls (PBS and PVXNi) were apparent (p<0.05 based on ANOVA test; FIG. 3B). Even though there was no significant difference between PVX-HisTRAIL and HisTRAIL, we could observe a trend indicating more effective inhibition from the conjugate nanoparticle over HisTRAIL alone (FIGS. 3A and B). Representative images of exercised tumors from each group are shown in FIG. 3C, in which the smallest is dissected from a mouse treated by PVX-HisTRAIL at the end of treatment. Even though not as effective as the conjugate formulate, HisTRAIL also showed effective inhibition resulting in a significantly smaller size compared to the controls (FIG. 3C). Together our data indicate that the PVX-delivered TRAIL outperforms free TRAIL and as such may be a promising candidate for further clinical development for applications in TNBC therapy.

In conclusion, we demonstrated the use of potato virus X, a naturally occurring platform with a flexuous filamentous nanostructure for TRAIL-presentation and delivery, mimicking membrane-bound TRAIL. The natural biologic can be produced easily through farming, with an excellent monodispersity and reproducibility. In addition, PVX is biocompatible, biodegradable, and non-infectious to mammals, adding another safety layer for future use as nanomedicine. We show in our developed protocol that PVX with displayed Ni-NTA can incorporate TRAIL with N-terminal His-tag by simply mixing at a 1:900 (particle: protein) molar ratio. Up to 490 molecules were displayed on PVX, i.e., there is one TRAIL molecule displayed in every three PVX CPs, indicating the high payload capability of PVX. The loading yield here is comparable with our established genetic modification method for preparing particle displaying proteins. It should be noted that the PVX-HisTRAIL suspension showed good stability with no apparent aggregation of disassembly for at least two weeks when stored at 4° C. in aqueous buffer conditions. When tested in a panel of TNBC cell lines, PVX-HisTRAIL shows 3-10-fold enhanced cell-killing effects to HisTRAIL alone in vitro. The conjugate also effectively inhibited tumor growth in an athymic nude mouse model of TNBC when injected intratumorally. Together these data suggest that PVX-TRAIL is a promising candidate for further clinical development and potential TNBC therapy.

Preparation of Potato Virus X (PVX) Displaying Nickel-Coordinated Nitrilotriacetic Acid (PVX-Ni)

PVX was propagated in *Nicotiana benthamiana* plants and purified according to our established protocol. About 20 mg of PVX particles were obtained from 100 g infected leaves. We developed a conjugation method to display nickel-coordinated nitrilotriacetic acid (Ni-NTA) as shown in FIG. 5. PVX displaying Ni-NTA is denoted as PVX-Ni. PVX displays surface lysine side chains amenable for chemical modification; the following protocols were established: Mixtures of PVX and the heterobifunctional linker NHS-PEG4-azide (Thermo Fisher Scientific) were prepared at a 1:10 (PVX coat protein:linker) molar ratio in 10 mM potassium phosphate buffer (KP buffer, pH 7.0) (reaction (i)). The final concentration of PVX was adjusted to 2 mg mL$^{-1}$. The reaction was carried out at room temperature for four hours to obtain PVX displaying azido groups (PVX-N$_3$). The excess linkers were removed by dialysis in KP buffer for five to six hours. The concentration of the resulting PVX-Ni was determined from the absorbance at 260 nm, read on a Nanodrop 2000 UV/visible spectrometer (Thermo Fisher), and calculated using the Beer-Lambert law and PVX-specific extinction coefficient (2.97 mL mg$^{-1}$ cm$^{-1}$ at 260 nm).

Meanwhile, $N_\alpha,N_\alpha$-bis(carboxymethyl)-L-lysine powder (NTA-Lys, Sigma-Aldrich) was dissolved in KP buffer to yield a 10 mg mL$^{-1}$ solution; the pH of the solution was adjusted to ~7.0 before the conjugation reaction, determined by pH paper. The linker propargyl-N-hydroxysuccinimidyl ester (100 mg mL$^{-1}$ in DMSO, Sigma Aldrich) was added at a 1:1 molar ratio and allowed to react with NTA-Lys on ice for five hours to obtain NTA with a terminal alkyne (propargyl-NTA) (reaction (ii)).

Prepared PVX-N$_3$ and propargyl-NTA were then mixed at a molar ratio of 1:10 to synthesize PVX with nitrilotriacetic groups (PVX-NTA). The required reagents needed for the click reaction were added in the following order: aminoguanidine (AMG, Sigma Aldrich) at 5 mM final concentration, CuSO$_4$:THPTA mix at 0.25:1.25 mM final concentration, and sodium ascorbate (Na Asc, Sigma Aldrich) at 5 mM final concentration. The reaction was allowed to proceed for 45 min at room temperature and terminated by addition of EDTA 0.5 M (reaction (iii)). The reaction mixture was then dialyzed against PBS buffer, pH 7.4 for five to six hours to remove excess NTA, click chemistry reagents, and EDTA.

To introduce Ni$^{2+}$ ions, PVX-NTA was dialyzed against PBS buffer, pH 7.4 containing 1 mM Ni$^{2+}$ overnight at room temperature (reaction (iv)). Excess Ni$^{2+}$ was removed by additional dialysis against PBS, pH 7.4 for five to six hours or longer to obtain the purified PVX-Ni. The PVX-Ni particle concentration was determined by Nanodrop as described above. To confirm the presence of Ni$^{2+}$ in the PVX-Ni formulation, PVX-Ni (2 mg mL$^{-1}$) was treated with 1,4-dithiothreitol (DTT, Gold Biotechnolohgy) at a 100 mM final concentration; presence of Ni$^{2+}$ is indicated by the solution turning into a yellow-brownish color, which is indicative of the reduction of Ni$^{2+}$ ions.

Plasmid Construction, Protein Expression, and Purification of TRAIL with an N-Terminal his-Tag (HisTRAIL)

A gene encoding the C-terminal extracellular region (aa 114-281) of human tumor necrosis factor-related apoptosis-inducing ligand (TRAIL), with NdeI and SacI restriction enzyme sites at the 5' and 3' ends, respectively, was synthesized by Integrated DN Technologies (IDT). The gene fragment was excised by double digestion enzymes (NdeI and SacI, purchased from NEB) and inserted into pET-28a (+) vector at the corresponding sites to yield pET-28a(+)/ HisTRAIL, which was subsequently transformed into Clear *Coli* BL21DE3 for expression. The expressed protein has a N-terminal His-tag, followed by a thrombin cleavage sequence, and a C-terminal bioactive human TRAIL (aa 114-281), denoted as HisTRAIL (FIG. 6A).

Figure 6B:
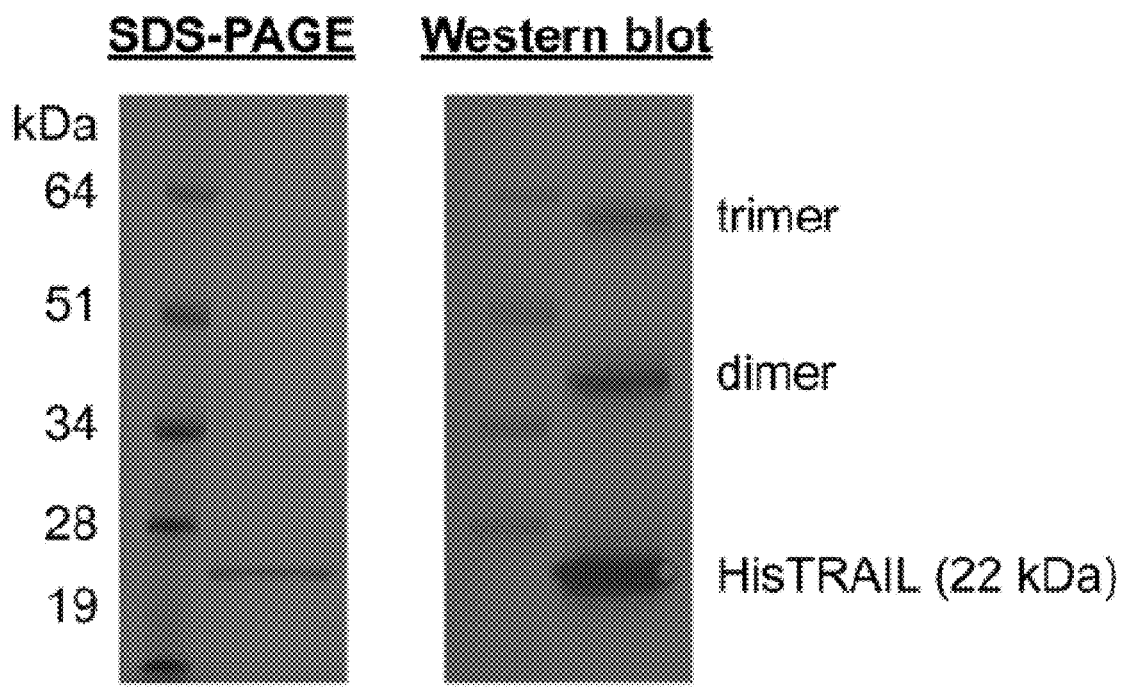

Bacteria were inoculated in Luria-Bertani (LB) medium supplemented with kanamycin (GOLDBIO) at 50 µg mL$^{-1}$ final concentration at 37° C.; the culture was grown until an OD600 of 0.8 was reached 0.8. The culture was then induced with isopropyl 3-D-thiogalactoside (IPTG, GOLDBIO) at 1 mM final concentration, culture growth was allowed to procced overnight at 22° C. to induce protein expression. Cells were then harvested by centrifugation (5,000×g, 10 min, 4° C.); the pellet was resuspended in bacterial cell lysis buffer (GOLDBIO) containing lysozyme (GOLDBIO) at 1 mg mL$^1$ final concentration, and DNase I (NEB). Cell lysis was conducted at 37° C. for 60 min. After centrifugation (13,000×g, 30 min, 4° C.) to remove cell debris, the supernatant containing HisTRAIL was collected. Protein purification was carried out using HisPur™ Ni-NTA resin (Thermo Fisher Scientific) for immobilized metal affinity chromatography, the protocol was according to the manufacturer's instructions. Eluted HisTRAIL in PBS buffer, pH 7.4 containing 250 mM imidazole was treated with DTT at room temperature for 1 h (to reduce disulfide bonds), and then dialyzed against PBS buffer, pH 7.4 overnight. The protein concentration was measured using a Nanodrop 2000 UV/visible spectrometer. The extinction coefficient of HisTRAIL was calculated as 27,390 $M^{-1}$ $cm^{-1}$ at 280 nm using ProtParam tool (https://web.expasy.org/protparam/) based on the number of tryptophan, tyrosine, and cysteine. HisTRAIL expression and purification was confirmed by denaturing gel electrophoresis (SDS-PAGE) and western blot using rabbit polyclonal anti-TRAIL primary antibody (Biovision). The analysis results are shown in FIG. 6B. A single band at 22 kDa was observed in SDS-PAGE gel after Coomassie Blue (CB) staining, indicative of purified HisTRAIL. In western blot, multiple bands derived from HisTRAIL oligomers were detected, reflecting the more sensitive detection of western blot vs. SDS PAGE.

Fluorescent Labeling of HisTRAIL

Water soluble sulfo-cyanine 5 NHS ester (Cy5, Lumiprobe) was added to HisTRAIL (0.5 mg $mL^{-1}$) at a 1:1 molar excess and the reaction was allowed to proceed for 2 h at room temperature; this reaction is designed to label TRAIL at lysine side chains. Excess fluorophores were then removed using PD-10 columns (GE Healthcare) and additional dialysis overnight at 4° C. Fluorescently labeled HisTRAIL-Cy5 was analyzed by SDS-PAGE and visualized upon excitation at 632 nm to detect Cy5 and under white light after CB staining to detect the protein. Co-localization of the fluorescent and protein band indicates covalent modification of HisTRAIL with Cy5 (FIG. Å 7A). The number of Cy5 per HisTRAIL was calculated using the Beer-Lambert law and the HisTRAIL- and Cy5-specific extinction coefficients (27,390 $M^{-1}$ $cm^{-1}$ at 280 nm and 271,000 $M^{-1}$ $cm^{-1}$ at 647 nm, respectively). It was determined that in every 4.6 HisTRAIL molecules were modified by a Cy5 molecule.

Size Exclusion Chromatography (SEC)

The particles (native PVX, PVX-Ni or PVX-HisTRAIL-Cy5) or the protein (HisTRAIL-Cy5) in PBS buffer, pH 7.4 were analyzed by SEC using a Superose6 column on the ÅKTA Explorer chromatography system (GE Healthcare). The flow rate was set at 0.5 mL·$min^{-1}$. For detection of fluorescent molecules or macromolecules, the absorbance at 260 nm (RNA), 280 nm (protein), and 647 nm (Cy5) was recorded.

SEC Profile of the Native PVX Particle

FIG. 8 shows the SEC profile of native PVX particle eluting from the column at 14.5 mL, which is identical to the elution peaks of PVX-Ni and PVX-HisTRAIL-Cy5 in FIG. 1B, confirming the intact filamentous structures of the PVX-based nanoplatforms after modification and purification.

Agarose Gel Electrophoresis

A 0.8% (w/v) agarose gel in TBE buffer was prepared for gel electrophoresis. Samples (5 μg PVX-Ni or PVX-HisTRAIL-Cy5 and 1 μg HisTRAIL-Cy5) were loaded and run at 100 V for 40 min in TBE buffer. Gels were imaged under epi-excitation at 632 nm (red) in the FluorChem R system instrument (ProteinSimple) for detection of fluorescently labeled protein or particle. Gels were then stained with CB and imaged under white light using FluorChem R system instrument.

Biotinylation of HisTRAIL

Similar to the method for labeling with Cy5 probe, a 1:1 molar ratio of biotin N-hydroxysuccinimide ester (MedChem Express) was to HisTRAIL (0.5 mg mL-1) for a 2-hour reaction at room temperature in a buffer. Free biotin was removed using a 10-kDa cutoff spin filter (10 washes with buffer). Biotin-conjugated HisTRAIL was analyzed by SDS-PAGE and western blot to assess the degree of biotinylation. Denatured HisTRAIL-biotin, after separation by SDS-PAGE, was transferred onto a nitrocellulose membrane (Thermo Scientific), and blocked for 60 min using 5% (w/v) skim milk powder dissolved in 0.1 M Tris-buffered saline containing 0.05% Tween 20 (TBST). To detect biotinylated HisTRAIL, alkaline phosphatase-conjugated streptavidin (Sigma Aldrich) diluted in 5% milk in TBST at a 1:500 ratio. BCIP/NBT substrate (Invitrogen) for alkaline phosphatase was added for visualization of biotinylated protein HisTRAIL-biotin (FIG. 7).

Transmission Electron Microscopy (TEM) and Immunostaining

TEM was used to confirm the filamentous structure of PVX-HisTRAIL-biotin. In addition, immunostaining was performed to further confirm biotinylation of PVX-HisTRAIL-biotin. The sample PVX-HisTRAIL-biotin controls (0.1 mg $mL^{-1}$) was loaded onto a carbon-coated copper grid, followed by fixation in 2.5% (v/v) glutaraldehyde solution for 10 min at room temperature. PVX-HisTRAIL biotin was then washed by PBS buffer and blocked in 1% (w/v) bovine serum albumin (BSA) in PBS containing 0.1% (v/v) Tween 20 for 30 min. Samples were equilibrated with 0.1% (w/v) BSA for 5 min and then stained with 10 nm-gold nanoparticles conjugated with anti-biotin antibodies (AURION) diluted 5 times in PBS buffer. PVX-Ni was prepared at the same procedures for control. All samples were stained by 2% (w/v) uranyl acetate for 1 min for imaging. TEM imaging was conducted using an FEI Tecnai F30 transmission electron microscope operated at 300 kV.

Denaturing Gel Electrophoresis, SDS-PAGE

Denatured protein samples (5 μg) in the presence of reducing reagent DTT were loaded on a 4-12% NuPAGE gel (Life Technologies) in 1×MOPS running buffer. The electrophoresis was conducted at constant voltage (200 V) for 35 min. Protein bands were visualized by CB staining under white light in FluoroChem R imaging instrument. Band thickness analysis were analyzed by ImageJ 1.47d (http://imagej.nih.gov/ij) to determine the weight ratio between HisTRAIL and PVX CP.

Fluorescent Western Blot

PVX-HisTRAIL was loaded in denaturing condition with DTT at the original concentration or 10× dilution to adjust the detected protein amount lying within linear detection ranges of standard curves. Various PVX or HisTRAIL loads were loaded at the same time for making standard curve. Protein concentrations were determined by Bradford assay kit (Biorad). For PVX standard curve, 0.1, 0.25, 0.5, 1 μg particles were loaded. For HisTRAIL standard curve, the protein was loaded at 0.25, 0.5, 1, 2.5, and 5 μg. Denatured samples after separating by SDS-PAGE, were transferred onto a nitrocellulose membrane (Thermo Scientific) using NuPAGE Transfer Buffer (Invitrogen). Blocking was conducted in 0.1M Tris-buffered saline (TBS, pH 7.6) containing 5% (w/v) milk and 0.05% (v/v) Tween 20. PVX and HisTRAIL was first recognized by rabbit anti-PVX and anti-TRAIL primary antibodies (Biovision), followed by detection from anti-rabbit secondary antibody conjugated with IRDye 800 CW (774/789 nm) (LICOR). The membrane was visualized under Infrared light; the fluorescence intensities were measured by FluoroChem R imaging instrument.

Cell Culture

Triple negative breast cancer cell lines MDA-MB-231, HCC-38, and BT-549 cell lines (provided by Prof. Ruth Keri, Case Western Reserve University) and HER-2 amplified breast cancer cell line SK-BR-3 (ATCC). MDA-MB- 231, HCC-38, BT-549, and SK-BR-3 were cultured in Dulbecco's modified Eagle's medium (DMEM) and Roswell Park Memorial Institute (RPMI) 1640 medium without or with insulin (0.023 IU/mL final concentration), and McCoy's 5A medium, respectively. All media were supplemented with 10% (v/v) fetal bovine serum (FBS) and 1% (v/v) penicillin/streptomycin. All cells were maintained at 37° C. and 5% $CO_2$.

MTT Cytotoxicity Assay

Cells (MDA-MB-231, HCC-38, BT-549, and SK-BR-3) were seeded at 5,000 cells per well in culture medium in 96-well plates 1 day prior to treatment. The next day, cells were treated with HisTRAIL or PVX-HisTRAIL at 1, 5, 10, 25, 50, 100, 250, 500 ng/mL normalized to TRAIL for 12 h in medium at 37° C. and 5% $CO_2$. Samples were prepared in triplicate and each assay was performed at least twice. PVX-Ni was added at the particle concentration matching the highest dose of PVX-HisTRAIL as a control to assess carrier toxicity (or lack thereof). Following incubation, cells were washed with PBS, pH 7.4 and fresh medium was replenished; then 10 μL MTT reagent was added as per manufacturer's instructions. Absorbance was determined using the Tecan infinite-M200 plate reader.

In Vitro Treatment Efficacy in SK-BR-3, a HER-2 Expressing Breast Cancer Model

Determination of levels of activated caspase-8 and caspase-3/7 MDA-MB-231 cells were seeded at 5,000 cells per well in a white-walled 96-well luminometer microplate one day prior to treatment. The next day, DMEM medium containing HisTRAIL or PVX-HisTRAIL (20 ng $mL^{-1}$) was exchanged and the cells were treated in 3 h. Non-treated cells were used as control. Samples were prepared in triplicate. Caspase-Glo 8 assay kit and Caspase-Glo 3/7 assay kit (Promega) were used to determine the level of activated caspases. Briefly, the reagent causes cell lysis, followed by caspase cleavage of the substrate and aminoluciferin which produces a luminescent signal in the presence of luciferase and ATP from the kit. Luminescence was read by the Tecan infinite-M200 plate reader to determine the proportional activated level of caspase 8- and 3/7.

In Vivo Treatment Efficacy Using the MDA-MB-231 Model

The animal study was carried using an IACUC-approved protocol. Female NCR nu/nu mice (6-8 weeks old) were injected subcutaneously into the right flank with $2\times10^6$ cells suspended in 100 μL of media and Matrigel (Corning) at a 1:1 ratio. Treatment was started when tumor volume reached 100-150 $mm^3$. Mice were randomly assigned to groups including PBS- (n=4), PVX-Ni-(n=4), HisTRAIL- (n=5), and PVX-HisTRAIL-treated groups (n=6). Freshly prepared HisTRAIL or PVX-HisTRAIL was injected intratumorally at a dose of 5 μL therapeutic protein per injection. PBS and PVX-Ni, at the corresponding content of particle in the conjugate, were used as controls. Tumors were measured daily and the volume was calculated using the formula $v=(l\times w^2)/2$, where l is the length and w is the width of tumor. Mice were also weighted to monitor potential side effects. All mice were euthanized and tumors were collected at the end of the study for imaging. All results are expressed as means±SD, calculated by GraphPad Prism. Statistical comparisons were made using one-way ANOVA. Differences between each group were considered significant at P value <0.05.

Example 2

Treatment of Triple Negative Breast Cancer

We describe the synthesis and preclinical testing of an epidermal growth factor receptor (EGFR)-targeted stealth filament to deliver TRAIL. EGFR is expressed on tumor cells and tumor endothelium, making it an attractive molecular target to direct nanocarriers to solid tumors and metastatic sites. EGFR is overexpressed in a subset of TNBC as well as a variety of human malignancies; it is considered an important molecular target. A link between EGFR expression and TRAIL sensitivity has been established, therefore further supporting the choice of targeting strategy. To test our hypothesis that surface-presentation and EGFR-targeting enhances TRAIL efficacy, we will fulfill the following aims: Determine specificity and efficacy of TRAIL filaments in vitro.

TRAIL will be presented on the surface of PVX as N-terminal coat protein fusion, then, EGFR-ligands will be conjugated via intervening PEG spacers. Genetic display of TRAIL on the PVX platform will streamline scaled up nanomanufacturing of the protein drug-nanoparticle in plants. Post-harvest chemical modification will be added: PEG will enhance pharmacokinetics and reduce immune recognition. The EGFR-targeting strategy will enhance tissue-specificity and targeted delivery. Cell target specificity and efficacy will be established using a panel of TNBC cancer cells and non-target immune cells. These studies will provide mechanistic insights into target-specificity vs. evasion from the mononuclear phagocyte system. Cell viability will be assessed; the IC50 will be determined and compared to free drug.

Evaluation of Tumor Homing and Efficacy In Vivo

We propose to evaluate the efficacy of TRAIL-conjugated stealth filaments using MDA-MB-231 xenografts induced through orthotopic injection of cells into the mammary fat pad of NCR nu/nu athymic mice. The MDA-MB-231 model has high relevance to triple negative breast cancer, and the cells express EGFR. Tumor targeting will be assessed in the setting of biodistribution and pharmacokinetics. We hypothesize that filamentous platform will extravasate and diffuse into the tumor tissue, therefore increasing the therapeutic index. Further, we hypothesize that targeted, multivalent, and surface-bound TRAIL presentation will increase its efficacy vs. soluble TRAIL.

Example 3

Treatment of Ovarian Cancer

Patients with ovarian cancer present at an advanced stage, with widely metastatic disease within the peritoneal cavity, and more than 90% of all patients will die of the disease. Platinum-based drugs are first line chemotherapies to treat ovarian cancer. However, the clinical utility of chemotherapy is limited based on the high toxicity and resulting adverse effects. Nanoparticle delivery systems increase safety; however, development of drug resistance remains a major barrier to clinical success. Inefficient cell kill can lead to recurrence of cancer in a more aggressive form that can resist a broad spectrum of therapeutics. More efficient delivery systems that target potent therapeutics are required to improve efficacy against tumors prone to resistance against contemporary treatments.

We propose the delivery of a platinum-based monotherapy and its combination with a death receptor ligand using a bio-inspired nanotechnology. This proposal builds on our recent development of a nanotechnology using the nucleoprotein components of the tobacco mosaic virus (TMV) to encapsulate and deliver large payloads of phenanthriplatin to ovarian cancer cells. Phenanthriplatin is a monofunctional Pt(II) compound that is 40× more potent compared to FDA-approved cisplatin, carboplatin, and oxalatoplatin therapies. Capitalizing on the potency of the phenanthriplatin-delivery system, this proposal sets out to evaluate the efficacy of the approach using mouse models of ovarian cancer. We will evaluate therapy success using phenanthriplatin monotherapy and its combination with tumor necrosis factor-related apoptosis-inducing ligand (TRAIL) therapy. TRAIL is a protein drug that interacts with death receptors to activate apoptotic pathways selectively in cancer cells. The combination of TRAIL and platinum-based drugs has shown to potentiate therapy success in the setting of ovarian cancer. Siervo-Sassi et al., Cancer Lett., 190:61-72 (2003); Cuello et al., Gynecol Oncol., 81:380-90 (2001). However, challenges exist: soluble TRAIL does not achieve the level of efficacy obtained with membrane-bound TRAIL. Therefore, we propose multivalent and surface-bound presentation of TRAIL using our nanoparticle platform.

The innovative aspects of this proposal lie in the bio-inspired nanotechnology, the delivery of the highly potent phenanthriplatin, and its combination with multivalent, surface-bound TRAIL. Mounting evidence suggests that high-aspect ratio materials, like TMV, have improved tumor targeting, while exhibiting enhanced tumor residence and deep penetration relative to their spherical counterparts. We have shown that aspect ratio-engineering can be used as a design parameter to produce nanoparticles with enhanced tumor-targeting properties. Building on these exciting results, this proposal sets out to evaluate the performance of the drug delivery system in the setting of ovarian cancer. We will fulfill the following:

Determine Specificity and Efficacy of Phenanthriplatin-Loaded TMV In Vitro.

Phenanthriplatin-loaded TMV will be synthesized using our established methods; formulations of distinct aspect ratio and molecular recognition chemistry will be developed and tested, because our supporting data indicate increased tumor cell targeting as a function of aspect ratio and surface chemistry. Ovarian cancer cell target specificity and efficacy will be determined and correlated with the engineered nanocarrier properties and phenanthriplatin loading and release profiles; off-target effects in mononuclear phagocyte cells will be monitored. The in vitro studies will provide baseline information for in vivo dosing.

Preclinical Testing of Phenanthriplatin-Loaded TMV to Determine Specificity, Efficacy and Off-Target Effects The in vivo profiles of phenanthriplatin-loaded TMV will be evaluated using 1) a syngeneic mouse model, in which tumors will be established in immune-competent mice using ID8 cells or hyper-aggressive ID8vegf/defb29 cells and C57B16 mice, and 2) patient-derived xenograft models. Free phenanthriplatin and cisplatin will be used as benchmarks against which the phenanthriplatin-loaded TMV will be compared.

Evaluate Phenanthriplatin-TRAIL Combination Therapies

We will develop TRAIL-displaying TMV, because multivalent and surface-bound-presentation of TRAIL is expected to enhance its efficacy. The phenanthriplatin-TRAIL combination therapy will be evaluated in vitro and in preclinical mouse models of ovarian cancer of metastatic and drug-resistant disease. We hypothesize that targeted delivery of phenanthriplatin in combination with membrane-bound TRAIL therapy will enable the treatment of otherwise difficult to treat ovarian cancer.

The complete disclosure of all patents, patent applications, and publications, and electronically available materials cited herein are incorporated by reference. The foregoing detailed description and examples have been given for clarity of understanding only. No unnecessary limitations are to be understood therefrom. In particular, the inventors are not bound by theories described herein. The invention is not limited to the exact details shown and described, for variations obvious to one skilled in the art will be included within the invention defined by the claims.

What is claimed is:

1. A method of treating tumor necrosis factor (TNF)-related apoptosis-inducing ligand (TRAIL)-sensitive cancer in a subject in need thereof, comprising administering to the subject a therapeutically effective amount of an agent comprising a potato virus X (PVX) plant virus particle or virus-like particle (VLP) which is non-covalently conjugated via a nickel-coordinated nitrilotriacetic acid (Ni-NTA) module to at least one TRAIL by coordination bonds between the Ni-NTA modules displayed on the PVX plant virus particle or VLP outer surface and a histidine-tag on TRAIL.

2. The method of claim 1, wherein the PVX plant virus particle or VLP is further loaded with or conjugated to one or more of an imaging agent, an anticancer agent, or a targeting agent.

3. The method of claim 2, wherein the targeting agent is a ligand for a tumor-associated receptor.

4. The method of claim 3, wherein the ligand is an epidermal growth factor receptor (EGFR) ligand.

5. The method of claim 1, wherein the plant virus particle or VLP is PEGylated.

6. The method of claim 2, wherein the anticancer agent is a platinum-based anticancer agent.

7. The method of claim 6, wherein the platinum-based anticancer agent is phenanthriplatin.

8. The method of claim 2, wherein the anticancer agent is doxorubicin.

9. The method of claim 2, wherein the imaging agent is a fluorescent molecule for fluorescent imaging.

10. The method of claim 2, wherein the PVX plant virus particle or VLP is loaded with or conjugated to an imaging agent, the method further comprising the step of imaging cancer tissue in the subject using an imaging device subsequent to administering the agent comprising the PVX plant virus particle or VLP.

11. The method of claim 1, wherein the cancer is selected from the group consisting of breast cancer, ovarian cancer, soft-tissue sarcoma, pancreatic cancer, colorectal cancer, non small cell lung cancer, lymphoma, non-Hodgkins lymphoma, and hepatocarcinoma.

12. The method of claim 1, wherein the cancer is triple negative breast cancer.

13. The method of claim 1, wherein the agent comprising the PVX plant virus particle or VLP is administered together with a pharmaceutically acceptable carrier.

14. The method of claim 1, wherein the therapeutically effective amount of the agent comprising the PVX plant virus particle or VLP is the amount required to activate caspase-dependent apoptosis via TRAIL-DR4/5 receptor binding in cancer cells of the subject.

15. The method of claim 1, wherein TRAIL is bound to the plant virus particle or VLP via N-terminus region of the ligand, providing display of C-terminus region for binding with death receptors on cancer cells.

16. The method of claim 1, wherein at least 100 TRAIL ligands are conjugated to the plant virus particle or VLP.

17. The method of claim 1, wherein TRAIL comprises trimers of TRAIL monomers.

* * * * *